United States Patent
Sigurdsson

(10) Patent No.: US 12,365,724 B2
(45) Date of Patent: Jul. 22, 2025

(54) ANTIBODIES BINDING TO PHOSPHO-TAU COMPRISING PHOSPHORYLATED Ser396 AND Ser404 AND METHODS OF DETECTING THEREOF

(71) Applicant: NEW YORK UNIVERSITY, New York, NY (US)

(72) Inventor: Einar M. Sigurdsson, Scarsdale, NY (US)

(73) Assignee: NEW YORK UNIVERSITY, New York, NY (US)

(*) Notice: Subject to any disclaimer, the term of this patent is extended or adjusted under 35 U.S.C. 154(b) by 881 days.

(21) Appl. No.: 17/312,854

(22) PCT Filed: Dec. 10, 2019

(86) PCT No.: PCT/US2019/065461
§ 371 (c)(1),
(2) Date: Jun. 10, 2021

(87) PCT Pub. No.: WO2020/123492
PCT Pub. Date: Jun. 18, 2020

(65) Prior Publication Data
US 2022/0041697 A1 Feb. 10, 2022

Related U.S. Application Data

(60) Provisional application No. 62/777,511, filed on Dec. 10, 2018.

(51) Int. Cl.
| | |
|---|---|
| *A61K 39/395* | (2006.01) |
| *A61K 39/00* | (2006.01) |
| *A61K 49/00* | (2006.01) |
| *A61P 25/28* | (2006.01) |
| *C07K 16/00* | (2006.01) |
| *C07K 16/18* | (2006.01) |

(52) U.S. Cl.
CPC .............. *C07K 16/18* (2013.01); *A61P 25/28* (2018.01); *C07K 2317/34* (2013.01); *C07K 2317/565* (2013.01)

(58) Field of Classification Search
CPC .......... C07K 2317/565; C07K 2317/76; C07K 2317/24; C07K 2317/56; C07K 2317/622; C07K 2317/54; C07K 2317/55; C07K 2317/52; C07K 2317/567; C07K 2317/51; C07K 2317/515; C07K 16/00; C07K 16/18; C07K 14/47; C07K 14/4711; A61K 39/0007; A61K 39/395; A61K 39/505; A61K 39/00; A61K 38/16; A61P 25/28; A61P 25/00; G01N 2800/28; G01N 2440/14; G01N 2800/2821; G01N 33/6896; G01N 2333/4709
See application file for complete search history.

(56) References Cited

U.S. PATENT DOCUMENTS

| | | | | |
|---|---|---|---|---|
| 8,012,936 | B2 * | 9/2011 | Sigurdsson | ........ A61K 39/3955 |
| | | | | 514/17.7 |
| 8,748,386 | B2 * | 6/2014 | Sigurdsson | ............. A61P 21/00 |
| | | | | 514/17.7 |
| 9,139,643 | B2 | 9/2015 | Sigurdsson et al. | |
| 9,777,056 | B2 | 10/2017 | Sigurdsson et al. | |
| 10,005,825 | B2 * | 6/2018 | Agadjanyan | ............ A61P 25/28 |
| 10,132,818 | B2 * | 11/2018 | Sigurdsson | ............. C07K 16/18 |
| 10,358,503 | B2 * | 7/2019 | Sigurdsson | ............. A61P 25/28 |
| 10,556,950 | B2 * | 2/2020 | Eguchi | .................... C07K 16/18 |
| 10,859,582 | B2 * | 12/2020 | Sigurdsson | ............. A61P 25/28 |
| 10,976,323 | B2 * | 4/2021 | Kirmess | ............. G01N 33/6848 |
| 11,124,552 | B2 * | 9/2021 | Ramsburg | ............ A61K 9/1271 |
| 11,519,920 | B2 * | 12/2022 | Sigurdsson | ........ A61K 49/0058 |

(Continued)

FOREIGN PATENT DOCUMENTS

| | | | | |
|---|---|---|---|---|
| WO | WO-9734145 | A1 * | 9/1997 | ......... C07K 14/4711 |
| WO | WO-2010144711 | A2 * | 12/2010 | ......... A61K 39/0005 |

(Continued)

OTHER PUBLICATIONS

MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*
International Search Report and Written Opinion for corresponding Application No. PCT/US2019/065461 (mailed Mar. 3, 2020).

(Continued)

*Primary Examiner* — Chang-Yu Wang
(74) *Attorney, Agent, or Firm* — Troutman Pepper Locke LLP (Rochester)

(57) ABSTRACT

The present invention relates to antibody-based molecules that are capable of preferentially and selectively binding to the C-terminal di-phosphorylated $^{\{p\}}$Ser396/$^{\{p\}}$Ser404 Tau peptide as well as to the $^{\{p\}}$Ser404 Tau peptide and the non-phosphorylated Tau peptide, but does not bind to the $^{\{p\}}$Ser396 Tau peptide. Such antibody-based molecules are useful to detect pathological Tau protein conformer if present in a biological sample, especially in conjunction with the diagnosis and/or treatment of Alzheimer's disease or other Tauopathy, and thus provide a diagnostic for Alzheimer's disease and other Tau pathologies. The antibody-based molecules of the present invention also have particular utility as prophylactic and therapeutic molecules for the treatment and/or prevention of Alzheimer's disease and related tauopathies.

18 Claims, 3 Drawing Sheets

Specification includes a Sequence Listing.

(56) References Cited

U.S. PATENT DOCUMENTS

| | | | |
|---|---|---|---|
| 11,773,148 B2* | 10/2023 | Wang | A61K 38/22 |
| | | | 424/185.1 |
| 11,787,854 B2 | 10/2023 | Sigurdsson et al. | |
| 11,958,898 B2 | 4/2024 | Sigurdsson | |
| 2008/0050383 A1* | 2/2008 | Sigurdsson | A61K 9/0019 |
| | | | 530/387.9 |
| 2011/0159013 A1 | 6/2011 | Acton et al. | |
| 2017/0183400 A1 | 6/2017 | Sigurdsson | |
| 2022/0041697 A1* | 2/2022 | Sigurdsson | A61P 25/16 |

FOREIGN PATENT DOCUMENTS

| | | | | |
|---|---|---|---|---|
| WO | 2017/011556 A1 | 1/2017 | | |
| WO | 2017/189963 A1 | 11/2017 | | |
| WO | 2018/011073 A1 | 1/2018 | | |
| WO | WO-2019084488 A1 * | 5/2019 | | A61K 39/0007 |

OTHER PUBLICATIONS

Gu et al., "Two Novel Tau Antibodies Targeting the 396/404 Region are Primarily Taken up by Neurons and Reduce Tau Protein Pathology," J. Biol. Chem. 288(46):33081-33095 (2013).

Congdon and Sigurdsson, "Tau-targeting Therapies for Alzheimer Disease," Nature Reviews Neurology 14(7):399-415 (2018).

Sigurdsson, "Tau Immunotherapies for Alzheimer's Disease and Related Tauopathies: Progress and Potential Pitfalls," Journal of Alzheimer's Disease 64:S555-S565 (2018).

* cited by examiner ion under 35 U.S.C. § 371 of PCT Application No. PCT/US2019/065461, filed Dec. 10, 2019, which claims the benefit of U.S. Provisional Patent Application Ser. No. 62/777,511, filed Dec. 10, 2018, which are hereby incorporated by reference in their entirety.

This invention was made with government support under R01 AG032611 and R01 NS077239 awarded by National Institutes of Health. The government has certain rights in the invention.

ANTIBODIES BINDING TO PHOSPHO-TAU COMPRISING PHOSPHORYLATED Ser396 AND Ser404 AND METHODS OF DETECTING THEREOF

This application is a national stage applicat

FIELD OF THE INVENTION

The present invention relates to antibody-based molecules, including full-length antibodies, epitope-binding domains thereof, and antibody derivatives that are capable of immunospecifically and selectively binding to the C-terminal di-phosphorylated $^{\{p\}}$Ser396/$^{\{p\}}$Ser404 Tau peptide as well as to the $^{\{p\}}$Ser404 Tau peptide and the non-phosphorylated Tau peptide.

BACKGROUND OF THE INVENTION

Alzheimer's disease is the most common form of dementia affecting more than 20 million people worldwide. Histopathologically, it is characterized by deposition of amyloid-β peptide and tau protein as well as loss of synapses and neurons. Currently, there are no treatments available that halt or slow the progression of the disease. Of tau targeting therapies in clinical trials, immunotherapies are the most common approach (Congdon E. E. and Sigurdsson, E. M., "Tau-targeting Therapies for Alzheimer Disease," *Nat. Rev. Neurol.* 14: 399-415 (2018)). Diagnosis of the disease, in particular at an early point, is troublesome and difficult and there exists a need for accurate diagnosis of tauopathies such as Alzheimer's disease. Antibody detection of abnormal Tau in cerebrospinal fluid has shown some promise (Blennow et al. "Cerebrospinal Fluid And Plasma Biomarkers In Alzheimer Disease," *Nat. Rev. Neurol.* 6: 131-144 (2010) and Weiner et al. "The Alzheimer's Disease Neuroimaging Initiative: A Review Of Papers Published Since Its Inception," *Alzheimer's. Dement.* 9: e111-e194 (2013)).

Over the years, antibody detection of phospho-Tau protein in cerebrospinal fluid has shown some utility for diagnosis of Alzheimer's disease (Blennow, K. et al. "Cerebrospinal Fluid And Plasma Biomarkers In Alzheimer Disease," *Nat. Rev. Neurol.* 6, 131-144 (2010); Lewis, J. et al. "Neurofibrillary Tangles, Amyotrophy And Progressive Motor Disturbance In Mice Expressing Mutant (P301L) Tau Protein," *Nat. Genet.* 25: 402-405; Weiner et al. "The Alzheimer's Disease Neuroimaging Initiative: A Review Of Papers Published Since Its Inception," *Alzheimers. Dement.* 9: e111-e194 (2013)), suggesting that further development in this arena is warranted (see, Congdon, E. E., "Harnessing The Immune System For Treatment And Detection Of Tau Pathology," *J. Alzheimers Dis.* 40:S113-S121 (2014)). However, CSF Tau levels in other tauopathies are usually not altered compared to controls (Theunis, C. et al. "Efficacy And Safety Of A Liposome-Based Vaccine Against Protein Tau, Assessed In Tau.P301L Mice That Model Tauopathy," *PLoS. One* 8: e72301 (2013); Hales et al. "From Frontotemporal Lobar Degeneration Pathology To Frontotemporal Lobar Degeneration Biomarkers," *Int. Rev. Psychiatry* 25:210-220 (2014)), and imaging dyes may not detect pathological Tau in all tauopathies (Fodero-Tavoletti et al. "Assessing THK523 Selectivity For Tau Deposits In Alzheimer's Disease And Non-Alzheimer's Disease Tauopathies," *Alzheimers. Res. Ther.* 6:11 (2014)). Imaging these Tau lesions in concert with amyloid-β (Aβ) is more likely to lead to accurate diagnosis as the regional pattern of Tau aggregates differs between the different tauopathies. Furthermore, all of them except Alzheimer's disease are in part defined by lack of Aβ deposition. In vivo imaging of Aβ plaques using compounds that bind well to β-sheets is already in clinical use (Mason et al. "Positron Emission Tomography Radioligands For In Vivo Imaging Of ABeta Plaques," *J. Labelled Comp. Radiopharm.* 56:89-95 (2013)). Several such dye-based Tau-binding ligands have been identified recently in preclinical studies and some of those are being evaluated (Fodero-Tavoletti et al. "Assessing THK523 Selectivity For Tau Deposits In Alzheimer's Disease And Non-Alzheimer's Disease Tauopathies," *Alzheimers. Res. Ther.* 6:11 (2014); Fodero-Tavoletti et al. "18F-THK523: A Novel In Vivo Tau Imaging Ligand For Alzheimer's Disease," *Brain* 134:1089-1100 (2011); Zhang et al. "A Highly Selective And Specific PET Tracer For Imaging Of Tau Pathologies," *J. Alzheimers. Dis.* 31:601-612 (2012); Chien et al. "Early Clinical PET Imaging Results With The Novel PHF-Tau Radioligand [F-18]-T807," *J. Alzheimers. Dis.* 34:457-468 (2013); Maruyama et al. "Imaging Of Tau Pathology In A Tauopathy Mouse Model And In Alzheimer Patients Compared To Normal Controls," *Neuron* 79:1094-1108 (2013); Okamura et al. "Quinoline And Benzimidazole Derivatives: Candidate Probes For In Vivo Imaging Of Tau Pathology In Alzheimer's Disease," *J. Neurosci.* 25:10857-10862 (2005); Harada et al. "Comparison Of The Binding Characteristics Of [18F]THK-523 And Other Amyloid Imaging Tracers To Alzheimer's Disease Pathology," *Eur. J. Nucl. Med. Mol. Imaging* 40:125-132 (2013); Ono et al. "Rhodanine And Thiohydantoin Derivatives For Detecting Tau Pathology In Alzheimer's Brains," *ACS Chem. Neurosci.* 2:269-275 (2011); Xia et al. "[(18)F]T807, A Novel Tau Positron Emission Tomography Imaging Agent For Alzheimer's Disease," *Alzheimers. Dement.* 9:666-676 (2013); Chien, D. T. "Early Clinical PET Imaging Results With The Novel PHF-Tau Radioligand [F18]-T808," *J. Alzheimers. Dis.* 38:171-184 (2014); Villemagne et al. "In Vivo Evaluation Of A Novel Tau Imaging Tracer For Alzheimer's Disease," *Eur. J. Nucl. Med. Mol. Imaging* 41:816-826 (2014); Okamura et al. "Non-Invasive Assessment Of Alzheimer's Disease Neurofibrillary Pathology Using 18F-THK5105 PET," *Brain* 137:1762-1771 (2014)). The hope and promise for Tau based ligands is that they will be better than Aβ ligands to monitor the status and progression of neurodegeneration. Antibody-based molecules are likely to provide greater specificity for detecting Tau lesions. In particular, smaller antibody fragments that bind to Tau are attractive as ligands for in vivo imaging to detect Tau lesions in patients with Alzheimer's disease or other tauopathies.

Within the cancer field, therapeutic antibodies have routinely been co-developed as imaging agents, and several such antibodies and Fab molecules are FDA approved for tumor imaging (Kaur et al. "Recent Trends In Antibody-Based Oncologic Imaging," *Cancer Lett.* 315: 97-111 (2012)).

The present invention is directed to overcoming these and other deficiencies in the art.

SUMMARY OF THE INVENTION

A first aspect of the present invention is directed to an antibody-based molecule that binds to an epitope of Tau. The epitope of Tau is present in the Tau sequence of TDHGAEIVYK{p}SPVVSGDT{p}SPRHL (SEQ ID NO:1). The antibody-based molecule of the present invention exhibits preferential binding to said Tau sequence when serine residues at positions 11 and 19 of SEQ ID NO: 1 are phosphorylated. The antibody-based molecule also binds to the Tau sequence when only the serine residue at position 19 is phosphorylated, and when neither residue is phosphorylated (i.e., an unphosphorylated Tau sequence). However, the antibody-based molecule does not bind to the Tau sequence when only the serine residue at position 11 is phosphorylated.

The antibody-based molecule of the present invention comprises any one, any two, any three, any four, any five, or any six of the following complementary determining regions: a heavy chain complementarity-determining region 1 (H-CDR1) having the amino acid sequence of SEQ ID NO: 2, or a modified amino acid sequence of SEQ ID NO: 2, said modified sequence containing 1 or 2 amino acid residue modifications as compared to SEQ ID NO: 2; a heavy chain complementarity-determining region 2 (H-CDR2) having the amino acid sequence of SEQ ID NO: 3, or a modified amino acid sequence of SEQ ID NO: 3, said modified sequence containing 1, 2, or 3 amino acid residue modifications as compared to SEQ ID NO: 3; a heavy chain complementarity-determining region 3 (H-CDR3) having the amino acid sequence of SEQ ID NO: 4, or a modified amino acid sequence of SEQ ID NO: 4, said modified sequence containing 1 or 2 amino acid residue modifications as compared to SEQ ID NO: 4; a light chain complementarity-determining region 1 (L-CDR1) having the amino acid sequence of SEQ ID NO: 5, or a modified amino acid sequence of SEQ ID NO: 5, said modified sequence containing 1, 2, or 3 amino acid residue modifications as compared to SEQ ID NO: 5; a light chain complementarity-determining region 2 (L-CDR2) having the amino acid sequence of SEQ ID NO: 6, or a modified amino acid sequence of SEQ ID NO: 6, said modified sequence containing 1 or 2 amino acid residue modifications as compared to SEQ ID NO: 6; and/or a light chain complementarity-determining region 3 (L-CDR3) having the amino acid sequence of SEQ ID NO: 7, or a modified amino acid sequence of SEQ ID NO: 7, said modified sequence containing 1 or 2 amino acid residue modifications as compared to SEQ ID NO: 7.

Another aspect of the present invention is directed to an isolated polynucleotide encoding the Tau antibody-based molecule described herein.

Another aspect of the present invention is directed to a pharmaceutical composition comprising the Tau antibody-based molecule as described herein, the isolated polynucleotide encoding the antibody-based molecule, or a vector comprising the isolated polynucleotide encoding the antibody-based molecule, and a pharmaceutically acceptable carrier.

Another aspect of the present invention is directed to a method of inhibiting onset of one or more symptoms of a condition involving pathological Tau protein in a subject. This method involves selecting a subject at risk of developing a condition involving pathological Tau protein and administering to the subject the pharmaceutical composition comprising the Tau antibody-based molecule as described herein or the polynucleotide encoding said molecule, where the composition is administered in an amount effective to inhibit onset of one or more symptoms of the condition involving pathological Tau protein in the subject.

Another aspect of the present invention is directed to a method of treating a condition involving a pathological Tau protein in a subject. This method involves selecting a subject having a condition involving a pathological Tau protein and administering to the subject the pharmaceutical composition comprising the Tau antibody-based molecule as described herein or the polynucleotide encoding said molecule in an amount effective to treat the condition involving pathological Tau protein in the subject.

Another aspect of the present invention is directed to a method of diagnosing Alzheimer's disease and/or a Tauopathy in a subject. This method involves detecting, in the subject, the presence of accumulated Tau protein using the antibody-based molecule of the present invention, and diagnosing Alzheimer's disease and/or Tauopathy in the subject based on said detecting.

Another aspect of the present invention is directed to a method of monitoring the progression of Alzheimer's disease or a Tauopathy in a subject. This method involves detecting, in the subject, the presence of accumulated Tau protein using the antibody-based molecule of the present invention; repeating the detecting periodically; and monitoring the progression of Alzheimer's disease or Tauopathy in the subject based on the repeated detection of accumulated Tau protein.

Another aspect of the present invention is directed to a diagnostic kit. The diagnostic kit of the present invention comprises the antibody-based molecule as described herein and a detectable label.

Another aspect of the present invention is directed to the use of the antibody-based molecule as described herein for detecting or measuring the presence or amount of said phosphorylated Tau protein in the brain, cerebrospinal fluid, blood, serum or plasma of a recipient subject.

Another aspect of the present invention is directed to an in vivo medicament for the treatment of Alzheimer's disease or another Tauopathy of a subject. This medicament comprises the antibody-based molecule as described herein in an amount effective to treat said Alzheimer's disease or other Tauopathy, and one or more carriers, diluents and/or stabilizers.

DETAILED DESCRIPTION OF THE INVENTION

Figure 1:
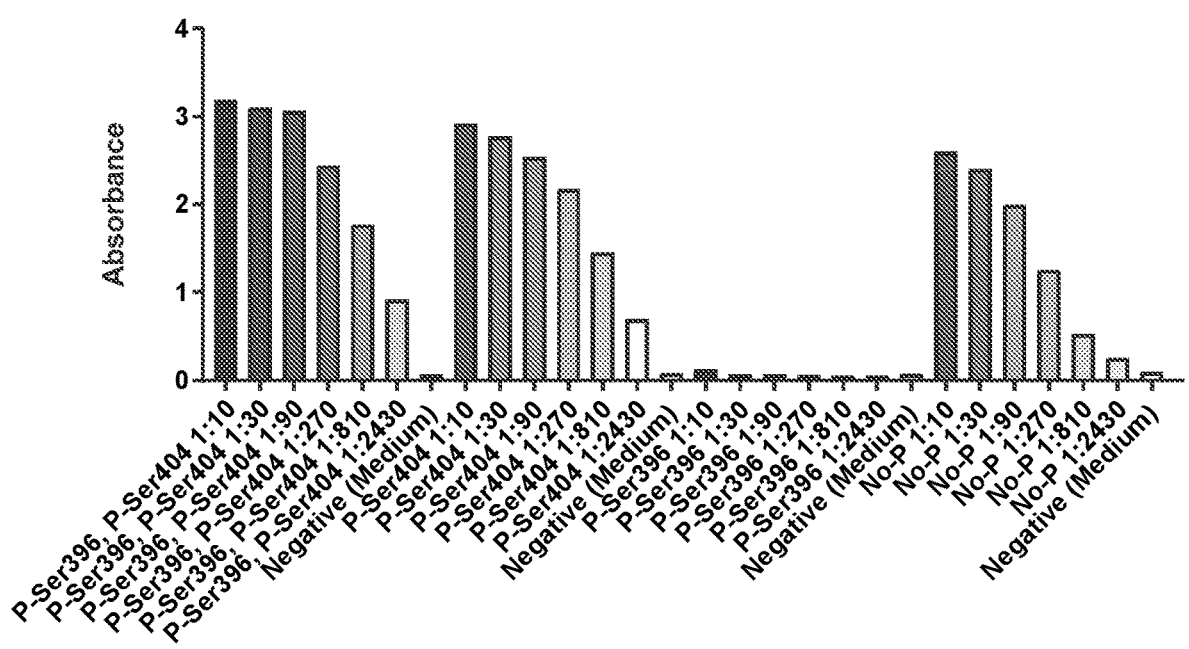
FIG. 1 shows binding of the 8B2D1 anti-Tau monoclonal antibody to its immunogen and related peptides. "P-Ser396, P-Ser404" is a Tau peptide fragment of having an amino acid sequence of SEQ ID NO:1, where serine residues at positions 11 and 19 of the fragment (corresponding to residues 396 and 404 of the full-length Tau protein (SEQ ID NO: 25)) are phosphorylated. "P-Ser404" is the same Tau peptide fragment of SEQ ID NO: 1, where only the serine residue at position 19 (corresponding to residue 404 of the full-length Tau) is phosphorylated. "P-Ser396" is the same Tau peptide of SEQ ID NO: 1, where only the serine residue at position 11 is phosphorylated. "No-P" is the same Tau fragment of SEQ ID NO:1 containing no phosphorylated serine residues.

The present invention relates to antibody-based molecules, including antibodies, epitope-binding domains thereof, and antibody derivative as described herein, that are capable of immunospecifically and selectively binding to particular phosphorylated and non-phosphorylated epitopes of Tau. Such antibody-based molecules are useful to detect pathological Tau protein conformer if present in a biological sample, especially in conjunction with the diagnosis and/or treatment of Alzheimer's disease or other Tauopathy, and thus provide a diagnostic for Alzheimer's disease and other Tau pathologies. The antibody-based molecules of the present invention also have prophylactic and therapeutic utility for the prevention and treatment of Alzheimer's disease and related tauopathies.

A first aspect of the present invention is directed to an antibody-based molecule that binds to an epitope of Tau. The epitope of Tau is present in the Tau sequence of TDHGAEIVYK$^{\{p\}}$SPVVSGDT$^{\{p\}}$SPRHL (SEQ ID NO:1). The antibody-based molecule of the present invention preferentially binds said Tau sequence when serine residues at positions 11 and 19 of SEQ ID NO: 1 are phosphorylated. These residues correspond to the serine residues at positions 396 and 404 of the full-length Tau protein (i.e., SEQ ID NO: 2 as described herein) and are alternatively referenced as Tau$^{\{p\}}$Ser396/$^{\{p\}}$Ser404. The antibody-based molecule of the present invention exhibits negligible binding to Tau when only the serine residue at position 11 of SEQ ID NO: 1 is phosphorylated (i.e., Tau$^{\{p\}}$Ser396).

The antibody-based molecule of the present invention also exhibits Tau binding when only the serine residue at position 19 of SEQ ID NO:1 is phosphorylated (i.e., Tau$^{\{p\}}$Ser404) and when neither serine residue at position 11 or 19 is phosphorylated (i.e., Tau Ser396/Ser404). Thus, the binding preference of the antibody-based molecule described herein is Tau$^{\{p\}}$Ser396/$^{\{p\}}$Ser404>Tau$^{\{p\}}$Ser404>Tau Ser396/Ser404>Tau$^{\{p\}}$Ser396.

As used herein, the term "Tau" is synonymous with the Tau protein and refers to any of the Tau protein isoforms (identified in, for example, UniProt as P10636, 1-9). Tau is a soluble microtubule-associated protein that is dynamically phosphorylated and dephosphorylated by a host of kinase enzymes during the cell cycle. Tau's ability to stabilize microtubules is dependent on the extent of its phosphorylation. In its dephosphorylated form, the protein is able to interact with tubulin to stabilize microtubules and promote tubulin assembly into microtubules (which form the cytoskeleton of the cell and are the major constituents of the mitotic spindles that pull apart eukaryotic chromosomes in mitosis). In its phosphorylated form, Tau is able to dissociate from microtubules, thereby permitting mitosis to occur. Thus, the phosphorylation of Tau acts as a direct microtubule association-dissociation switch within the neuron (Pedersen et al. "Tau Immunotherapy For Alzheimer's Disease," Trends Mol. Med. 21(6): 394-402 (2015), which is hereby incorporated by reference herein in its entirety).

The amino acid numbering of Tau residues provided herein is given with respect to SEQ ID NO: 25, as shown below, with methionine being the first amino acid residue thereof.

```
                                        (SEQ ID NO: 25)
MAEPRQEFEV  MEDHAGTYGL  GDRKDQGGYT  MHQDQEGDTD

AGLKESPLQT  PTEDGSEEPG  SETSDAKSTP  TAEDVTAPLV

DEGAPGKQAA  AQPHTEIPEG  TTAEEAGIGD  TPSLEDEAAG

HVTQARMVSK  SKDGTGSDDK  KAKGADGKTK  IATPRGAAPP

GQKGQANATR  IPAKTPPAPK  TPPSSGEPPK  SGDRSGYSSP

GSPGTPGSRS  RTPSLPTPPT  REPKKVAVVR  TPPKSPSSAK

SRLQTAPVPM  PDLKNVKSKI  GSTENLKHQP  GGGKVQIINK

KLDLSNVQSK  CGSKDNIKHV  PGGGSVQIVY  KPVDLSKVTS

KCGSLGNIHH  KPGGGQVEVK  SEKLDFKDRV  QSKIGSLDNI

THVPGGGNKK  IETHKLTFRE  NAKAKTDHGA  EIVYKSPVVS

GDTSPRHLSN  VSSTGSIDMV  DSPQLATLAD  EVSASLAKQG  L
```

The term "Phospho-Tau" or "P-Tau" refers to a Tau protein or peptide that has been phosphorylated at one or more serine or threonine residues. As used herein, the notation "$^{\{p\}}$Ser" or "$^{\{p\}}$S" denote the amino acid residue phosphoserine. For example, the notation "$^{\{p\}}$Ser396/$^{\{p\}}$Ser404" refers to a polypeptide portion of SEQ ID NO: 25 wherein the residues that correspond to residues 396 and 404 of SEQ ID NO: 25 (shown underlined above) are phosphoserine residues. In contrast, the notation "Ser396/Ser404" refers to a polypeptide portion of SEQ ID NO: 25 wherein the residues that correspond to residues 396 and 404 of SEQ ID NO: 25 are both non-phosphorylated serine residues. Thus, for example, the notation "$^{\{p\}}$Ser396/Ser404" refers to a polypeptide portion of Tau wherein the residue that corresponds to residue 396 of SEQ ID NO: 25 is a phosphoserine residue, and the residue that corresponds to residue 404 of SEQ ID NO: 25 is serine.

Hyperphosphorylation of Tau can result in the formation of insoluble self-assembling "tangles," referred to herein as "Tau aggregates," of paired helical filaments and straight filaments. Such Tau aggregates may be intracellular (e.g., intraneuronal), but may also form outside of the cells. The presence of Tau aggregates impairs Tau's ability to stabilize microtubules and thus leads to microtubule disassembly, dendritic spinal collapse, and the degeneration of axons. Normal Tau contains, on average two phosphorylated sites, whereas the hyperphosphorylated Tau filaments average seven to eight phosphorylated sites. Hyperphosphorylated Tau is the main constituent of the intracellular neurofibrillary tangles that are a main hallmark of Alzheimer's Disease and other tauopathies. As used herein, the term "pathological Tau" refers to Tau that has undergone conformational change associated with hyperphosphorylation and other posttranslational modifications, that tends to aggregate into oligomers, filaments and eventually neurofibrillary tangles. Pathological Tau is characteristic of Alzheimer's Disease and other tauopathies.

The "antibody-based molecules" of the present invention include antibodies that are capable of immunospecifically and selectively binding to pathological Tau as described herein. In particular, the antibody-based molecule of the present invention immunospecifically and selectively binds to the di-phosphorylated $^{\{p\}}$Ser396/$^{\{p\}}$Ser404 epitope of Tau, as well as to the $^{\{p\}}$Ser404 Tau peptide and the non-phosphorylated Tau peptide.

Antibody-based molecules include, without limitation full antibodies, epitope binding fragments of whole antibodies, and antibody derivatives. An epitope binding fragment of an antibody can be obtained through the actual fragmenting of a parental antibody (for example, a Fab or (Fab)$_2$ fragment). Alternatively, the epitope binding fragment is an amino acid sequence that comprises a portion of the amino acid sequence of such parental antibody. As used herein, a molecule is said to be a "derivative" of an antibody (or relevant portion thereof) if it is obtained through the actual chemical modification of a parent antibody or portion thereof, or if it comprises an amino acid sequence that is substantially similar to the amino acid sequence of such parental antibody or relevant portion thereof (for example, differing by less than 30%, less than 20%, less than 10%, or less than 5% from such parental molecule or such relevant portion thereof, or by 10 amino acid residues, or by fewer than 10, 9, 8, 7, 6, 5, 4, 3 or 2 amino acid residues from such parental molecule or relevant portion thereof).

An antibody of the present invention is an intact immunoglobulin as well as a molecule having an epitope-binding fragment thereof. As used herein, the terms "fragment", "region", and "domain" are generally intended to be synonymous, unless the context of their use indicates otherwise. Naturally occurring antibodies typically comprise a tetramer which is usually composed of at least two heavy (H) chains and at least two light (L) chains. Each heavy chain is comprised of a heavy chain variable ($V_H$) region and a heavy chain constant ($C_H$) region, usually comprised of three domains ($C_H1$, $C_H2$ and $C_H3$ domains). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable ($V_L$) region and a light chain constant ($C_L$) region. Light chains include kappa chains and lambda chains. The heavy and light chain variable regions are typically responsible for antigen recognition, while the heavy and light chain constant regions may mediate the binding of the immunoglobulin to host tissues or factors, including various cells of the immune system (e.g., effector cells) and the first component (C1q) of the classical complement system. The $V_H$ and $V_L$ regions can be further subdivided into regions of hypervariability, termed "complementarity determining regions," or "CDRs," that are interspersed with regions of more conserved sequence, termed "framework regions" (FR). Each $V_H$ and $V_L$ region is composed of three CDR domains and four FR domains arranged from amino-terminus to carboxy-terminus in the following order: FR1-CDR1-FR2-CDR2-FR3-CDR3-FR4. The variable regions of the heavy and light chains contain a binding domain that interacts with an antigen. Of particular relevance are antibodies and their epitope-binding fragments that have been "isolated" so as to exist in a physical milieu distinct from that in which it may occur in nature or that have been modified so as to differ from a naturally-occurring antibody in amino acid sequence.

Fragments of antibodies (including Fab and (Fab)$_2$ fragments) that exhibit epitope-binding ability can be obtained, for example, by protease cleavage of intact antibodies. Single domain antibody fragments possess only one variable domain (e.g., $V_L$ or $V_H$). Examples of the epitope-binding fragments encompassed within the present invention include (i) Fab' or Fab fragments, which are monovalent fragments containing the $V_L$, $V_H$, $C_L$ and $C_H1$ domains; (ii) F(ab')$_2$ fragments, which are bivalent fragments comprising two Fab fragments linked by a disulfide bridge at the hinge region; (iii) Fd fragments consisting essentially of the $V_H$ and $C_H1$ domains; (iv) Fv fragments consisting essentially of a $V_L$ and $V_H$ domain, (v) dAb fragments (Ward et al. "Binding Activities Of A Repertoire Of Single Immunoglobulin Variable Domains Secreted From *Escherichia coli*," *Nature* 341:544-546 (1989) which is hereby incorporated by reference in its entirety), which consist essentially of a $V_H$ or $V_L$ domain and also called domain antibodies (Holt et al. "Domain Antibodies: Proteins For Therapy," *Trends Biotechnol.* 21(11):484-490 (2003), which is hereby incorporated by reference in its entirety); (vi) camelid or nanobodies (Revets et al. "Nanobodies As Novel Agents For Cancer Therapy," *Expert Opin. Biol. Ther.* 5(1):111-124 (2005), which is hereby incorporated by reference in its entirety), and (vii) isolated complementarity determining regions (CDR). An epitope-binding fragment may contain 1, 2, 3, 4, 5 or all 6 of the CDR domains of such antibody.

Such antibody fragments are obtained using conventional techniques known to those of skill in the art. For example, F(ab')$_2$ fragments may be generated by treating a full-length antibody with pepsin. The resulting F(ab')$_2$ fragment may be treated to reduce disulfide bridges to produce Fab' fragments. Fab fragments may be obtained by treating an IgG antibody with papain and Fab' fragments may be obtained with pepsin digestion of IgG antibody. A Fab' fragment may be obtained by treating an F(ab')$_2$ fragment with a reducing agent, such as dithiothreitol. Antibody fragments may also be generated by expression of nucleic acids encoding such fragments in recombinant cells (see e.g., Evans et al. "Rapid Expression Of An Anti-Human C5 Chimeric Fab Utilizing A Vector That Replicates In COS And 293 Cells," *J. Immunol. Meth.* 184:123-38 (1995), which is hereby incorporated by reference in its entirety). For example, a chimeric gene encoding a portion of a F(ab')$_2$ fragment could include DNA sequences encoding the CH1 domain and hinge region of the heavy chain, followed by a translational stop codon to yield such a truncated antibody fragment molecule. Suitable fragments capable of binding to a desired epitope may be readily screened for utility in the same manner as an intact antibody.

Antibody derivatives include those molecules that contain at least one epitope-binding domain of an antibody, and are typically formed using recombinant techniques. One exemplary antibody derivative includes a single chain Fv (scFv). A scFv is formed from the two domains of the Fv fragment, the $V_L$ region and the $V_H$ region, which are encoded by separate gene. Such gene sequences or their encoding cDNA are joined, using recombinant methods, by a flexible linker (typically of about 10, 12, 15 or more amino acid residues) that enables them to be made as a single protein chain in which the $V_L$ and $V_H$ regions associate to form monovalent epitope-binding molecules (see e.g., Bird et al. "Single-Chain Antigen-Binding Proteins," *Science* 242:423-426 (1988); and Huston et al. "Protein Engineering Of Antibody Binding Sites: Recovery Of Specific Activity In An Anti-Digoxin Single-Chain Fv Analogue Produced In *Escherichia coli*," *Proc. Natl. Acad. Sci.* (*U.S.A.*) 85:5879-5883 (1988), which are hereby incorporated by reference in their entirety). Alternatively, by employing a flexible linker that is not too short (e.g., less than about 9 residues) to enable the $V_L$ and $V_H$ regions of a different single polypeptide chains to associate together, one can form a bispecific antibody, having binding specificity for two different epitopes.

In another embodiment, the antibody derivative is a divalent or bivalent single-chain variable fragment, engineered by linking two scFvs together either in tandem (i.e., tandem scFv), or such that they dimerize to form diabodies (Holliger et al. "'Diabodies': Small Bivalent And Bispecific Antibody Fragments," *Proc. Natl. Acad. Sci.* (*U.S.A.*) 90(14), 6444-8 (1993), which is hereby incorporated by reference in its entirety). In yet another embodiment, the antibody is a trivalent single chain variable fragment, engineered by linking three scFvs together, either in tandem or in a trimer formation to form triabodies. In another embodiment, the antibody is a tetrabody single chain variable fragment. In another embodiment, the antibody is a "linear antibody" which is an antibody comprising a pair of tandem Fd segments ($V_H$—$C_H$1-$V_H$—$C_H$1) that form a pair of antigen binding regions (see Zapata et al. *Protein Eng.* 8(10):1057-1062 (1995), which is hereby incorporated by reference in its entirety). In another embodiment, the antibody derivative is a minibody, consisting of the single-chain Fv regions coupled to the $C_H3$ region (i.e., scFv-$C_H3$).

These and other useful antibody fragments and derivative in the context of the present invention are discussed further herein. It also should be understood that the term antibody-based molecule, unless specified otherwise, also includes antibody-like polypeptides, such as chimeric antibodies and humanized antibodies, and antibody fragments retaining the ability to specifically bind to the antigen (epitope-binding fragments) provided by any known technique, such as enzymatic cleavage, peptide synthesis, and recombinant techniques.

An antibody as generated herein may be of any isotype. As used herein, "isotype" refers to the immunoglobulin class (for instance IgG1, IgG2, IgG3, IgG4, IgD, IgA, IgE, or IgM) that is encoded by heavy chain constant region genes. The choice of isotype typically will be guided by the desired effector functions, such as antibody-dependent cellular cytotoxicity (ADCC) induction. Exemplary isotypes are IgG1, IgG2, IgG3, and IgG4. Either of the human light chain constant regions, kappa or lambda, may be used. If desired, the class of an anti-Tau antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses.

In one embodiment, the antibody-based molecule is a monovalent antibody, preferably a monovalent antibody as described in PCT Publication WO 2007/059782 to Parren, which is hereby incorporated by reference in its entirety) having a deletion of the hinge region. Such an antibody may be constructed by a method comprising: i) providing a nucleic acid construct encoding the VL region of the anti-Tau antibody described herein and a nucleotide sequence encoding the constant CL region of an Ig, wherein said nucleotide sequence encoding the VL region of the anti-Tau antibody and said nucleotide sequence encoding the CL region of an Ig are operably linked together, and where, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the VH region of the anti-Tau antibody described herein and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, do not comprise any amino acid residues which participate in the formation of disulfide bonds or covalent or stable non-covalent inter-heavy chain bonds with other peptides comprising an identical amino acid sequence of the CH region of the human Ig in the presence of polyclonal human IgG or when administered to an animal human being, where said nucleotide sequence encoding the VH region of the Tau antibody as described herein and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii)

Similarly, in one embodiment, the antibody is a monovalent antibody, which comprises: (i) the VL or VH of the Tau antibody as described herein or an antigen-binding part of the said region, and (ii) a CH region of an immunoglobulin or a fragment thereof comprising the CH2 and CH3 regions, wherein the CH region or fragment thereof has been modified such that the region corresponding to the hinge region and, if the immunoglobulin is not an IgG4 subtype, other regions of the CH region, such as the CH3 region, do not comprise any amino acid residues, which are capable of forming disulfide bonds with an identical CH region or other covalent or stable non-covalent inter-heavy chain bonds with an identical CH region in the presence of polyclonal human IgG.

In a further embodiment, the heavy chain of the monovalent antibody has been modified such that the entire hinge has been deleted. In another embodiment, the sequence of said monovalent antibody has been modified so that it does not comprise any acceptor sites for N-linked glycosylation.

The term "epitope" as used herein refers to an antigenic determinant capable of being bound to an antibody. Epitopes usually comprise surface groupings of molecules such as amino acids or sugar side chains and usually have specific three dimensional structural characteristics, as well as specific charge characteristics. Conformational and non-conformational epitopes are distinguished in that the binding to the former, but not the latter, is lost in the presence of denaturing solvents. An epitope may comprise amino acid residues directly involved in the binding (also called the immunodominant component of the epitope) and other amino acid residues, which are not directly involved in the binding, such as amino acid residues that are effectively blocked by the specific antigen-binding peptide (in other words, the amino acid residue is within the footprint of the specific antigen-binding peptide).

The Tau antibody-based molecule of the present invention "immunospecifically" binds an epitope of Tau within SEQ ID NO: 1 more frequently, more rapidly, with greater duration and/or with greater affinity or avidity than an alternative epitope. In particular, the Tau antibody-based molecule as described herein binds immunospecifically to Tau containing $^{\{p\}}$Ser396/$^{\{p\}}$Ser404. The Tau antibody-based molecule as described herein also exhibits binding to Tau containing $^{\{p\}}$Ser404 and Tau containing unphosphorylated serine residues at positions 396 and 404 (i.e., Ser396/Ser404). The antibody-based molecule as described herein exhibits negligible binding to Tau containing only $^{\{p\}}$Ser396.

In accordance with the present invention, the antibody-based molecule of the present invention binds to its Tau epitope with an affinity corresponding to a $K_D$ of about $10^{-7}$ M or less, such as about $10^{-8}$ M or less, such as about $10^{-9}$ M or less when determined by, for instance, surface plasmon resonance (SPR) technology in a Biacore 3000 instrument (preferably using the antibody as the ligand and the antigen as the analyte). The Tau antibody-based molecule of the present invention binds to the Tau epitope with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., bovine serum albumin ("BSA"), casein, etc.). The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The term "$k_d$" ($sec^{-1}$ or 1/s), as used herein, refers to the dissociation rate constant of a particular antibody-antigen interaction. The value is also referred to as the $k_{off}$ value. The term "$k_a$" ($M^{-1} \times sec^{-1}$ or 1/M), as used herein, refers to the association rate constant of a particular antibody-antigen interaction. The term "$K_D$" (M), as used herein, refers to the dissociation equilibrium constant of a particular antibody-antigen interaction and is obtained by dividing the $k_d$ by the $k_a$. The term "$K_A$" ($M^{-8}$ or 1/M), as used herein, refers to the association equilibrium constant of a particular antibody-antigen interaction and is obtained by dividing the $k_a$ by the $k_d$.

The antibody-based molecule of the present invention binds "selectively" to Tau containing $^{\{p\}}$Ser396/$^{\{p\}}$Ser404>$^{\{p\}}$Ser404>Ser396/Ser404, which means in the context of the present invention that the antibody-based molecule of the present invention binds to Tau containing $^{\{p\}}$Ser396/$^{\{p\}}$Ser404 with a higher affinity than it binds to Tau containing $^{\{p\}}$Ser404 and Tau containing Ser396/Ser404. The antibody-based molecule described herein binds only negligibly to Tau containing only $^{\{p\}}$Ser396. Such higher affinity will be at least 10-fold higher, at least 30-fold higher, at least 100-fold higher, at least 300-fold higher, at least 1,000-fold higher, at least 3,000-fold higher, or at least 10,000-fold higher. The extent of "selectivity" of the antibody-based molecule described herein for Tau containing $^{\{p\}}$Ser396/$^{\{p\}}$Ser404, $^{\{p\}}$Ser404, or Ser396/Ser404 is determined by comparing, via ELISA or Biacore, the affinity with which the antibody-based molecule immunospecifically binds to the different Tau epitopes.

In one embodiment, the antibody-based molecules of the present invention are "humanized," particularly if they are to be employed for therapeutic purposes. The term "humanized" refers to a chimeric molecule, generally prepared using recombinant techniques, having an antigen-binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild-type (e.g., fully human) or they may be modified to contain one or more amino acid substitutions not found in the human antibody whose sequence has served as the basis for humanization. Humanization lessens or eliminates the likelihood that a constant region of the molecule will act as an immunogen in human individuals, but the possibility of an immune response to the foreign variable region remains (LoBuglio, A. F. et al. "Mouse/Human Chimeric Monoclonal Antibody In Man: Kinetics And Immune Response," *Proc. Natl. Acad. Sci. USA* 86:4220-4224 (1989), which is hereby incorporated by reference in its entirety). Another approach focuses not only on providing human-derived constant regions, but modifying the variable regions so as to reshape them as closely as possible to human form. The variable regions of both heavy and light chains contain three complementarity-determining regions (CDRs) which vary in response to the antigens in question and determine binding capability. The CDRs are flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from non-human antibody on the FRs present in the human antibody to be modified. Suitable methods for humanizing the non-human antibody described herein are known in the art see e.g., Sato, K. et al., *Cancer Res* 53:851-856 (1993); Riechmann, L. et al., "Reshaping Human Antibodies for Therapy," *Nature* 332:323-327 (1988); Verhoeyen, M. et al., "Reshaping Human Antibodies: Grafting An Antilysozyme Activity," *Science* 239:1534-1536 (1988); Kettleborough, C. A. et al., "Humanization Of A Mouse Monoclonal Antibody By CDR-Grafting: The Importance Of Framework Residues On Loop Conformation," *Protein Engineering* 4:773-3783 (1991); Maeda, H. et al., "Construction Of Reshaped Human Antibodies With HIV-Neutralizing Activity," *Human Antibodies Hybridoma* 2:124-134 (1991); Gorman, S. D. et al., "Reshaping A Therapeutic CD4 Antibody," *Proc. Natl. Acad. Sci. USA* 88:4181-4185 (1991); Tempest, P. R. et al., "Reshaping A Human Monoclonal Antibody To Inhibit Human Respiratory Syncytial Virus Infection In Vivo," *Bio Technology* 9:266-271 (1991); Co, M. S. et al., "Humanized Antibodies For Antiviral Therapy," *Proc. Natl. Acad. Sci. USA* 88:2869-2873 (1991); Carter, P. et al., "Humanization Of An Anti-p185her2 Antibody For Human Cancer Therapy," *Proc. Natl. Acad. Sci. USA* 89:4285-4289 (1992); and Co, M. S. et al., "Chimeric And Humanized Antibodies With Specificity For The CD33 Antigen," *J. Immunol.* 148:1149-1154 (1992), which are hereby incorporated by reference in their entirety. In some embodiments, humanized Tau antibodies of the present invention preserve all CDR sequences (for example, a humanized antibody containing all six CDRs from the mouse antibody). In other embodiments, humanized Tau antibodies of the present invention have one or more CDRs (one, two, three, four, five, six) which are altered with respect to the original antibody. Methods of humanizing an antibody are well-known in the art and suitable for humanizing the antibodies of the present invention (see, e.g., U.S. Pat. No. 5,225,539 to Winter; U.S. Pat. Nos. 5,530,101 and 5,585,089 to Queen and Selick; U.S. Pat. No. 5,859,205 to Robert et al.; U.S. Pat. No. 6,407,213 to Carter; and U.S. Pat. No. 6,881,557 to Foote, which are hereby incorporated by reference in their entirety).

In one embodiment, the Tau antibody-based molecule of the invention is a human antibody. Suitable human antibodies may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice."

The HuMAb mouse contains a human immunoglobulin gene minilocus that encodes unrearranged human heavy variable and constant (μ and Υ) and light variable and constant (Κ) chain immunoglobulin sequences, together with targeted mutations that inactivate the endogenous μ and Κ chain loci (Lonberg, N. et al., "Antigen-Specific Human Antibodies From Mice Comprising Four Distinct Genetic Modifications," *Nature* 368:856-859 (1994), which is hereby incorporated by reference in its entirety). Accordingly, such mice exhibit reduced expression of mouse IgM or IgK and in response to immunization, the introduced human heavy and light chain transgenes, undergo class switching and somatic mutation to generate high affinity human IgG, κ monoclonal antibodies (Lonberg, N. et al., "Antigen-Specific Human Antibodies From Mice Comprising Four Distinct Genetic Modifications," *Nature* 368:856-859 (1994); Lonberg, N., "Human Monoclonal Antibodies from Transgenic Mice," In: HANDBOOK EXPERIMENTAL PHARMACOLOGY, Volume 181 (Starke, K. et al., *Eds.*) Springer-Verlag Berlin Heidelberg (1994); Lonberg, N. et al., "Human Antibodies From Transgenic Mice," *Intern. Rev. Immunol.* 13(1): 65-93 (1995); Harding, F. et al., "Class Switching In Human Immunoglobulin Transgenic Mice," *Ann. N.Y. Acad. Sci* 764:536-546 (1995), which are hereby incorporated by reference in their entirety). The preparation of HuMAb mice and human antibodies using this mouse model which can be employed to generate human versions of the antibodies described herein are described in detail in Taylor, L. et al., "A Transgenic Mouse That Expresses A Diversity Of Human Sequence Heavy And Light Chain Immunoglobulins," *Nucl. Acids Res.* 20(23):6287-6295 (1992); Chen, J. et al., "Immunoglobulin Gene Rearrangement In B Cell Deficient Mice Generated By Targeted Deletion Of The JH Locus," *Int'l. Immunol.* 5:647-656 (1993); Tuaillon, N. et al., "Biased Utilization Of DHQ52 And JH4 Gene Segments In A Human Ig Transgenic Minilocus Is Independent Of Antigenic Selection," *J. Immunol.* 152:2912-2920 (1994); Taylor, L. et al., "Human Immunoglobulin Transgenes Undergo Rearrangement, Somatic Mutation And Class Switching In Mice That Lack Endogenous IgM," *Int'l. Immunol.* 6:579-591 (1994); Fishwild, D. et al., "High-Avidity Human IgG Kappa Monoclonal Antibodies From A Novel Strain Of Minilocus Transgenic Mice," *Nature Biotechnol.* 14:845-851 (1996); see also U.S. Pat. No. 5,545,806 to Lonberg and Kay; U.S. Pat. No. 5,569,825 to Lonberg and Kay; U.S. Pat. No. 5,625,126 to Lonberg and Kay; U.S. Pat. No. 5,633,425 to Lonberg and Kay; U.S. Pat. No. 5,789,650 to Lonberg and Kay; U.S. Pat. No. 5,877,397 to Lonberg and Kay; U.S. Pat. No. 5,661,016 to Lonberg and Kay; U.S. Pat. No. 5,814,318 to Lonberg and Kay; U.S. Pat. No. 5,874,299 to Lonberg and Kay; U.S. Pat. Nos. 5,770,429 5,770,429; and U.S. Pat. No. 5,545,807 to Surani; PCT Publications WO 98/24884, WO 94/25585, WO 93/1227, WO 92/22645, WO 92/03918 and WO 01/09187, which are hereby incorporated by reference in their entirety).

In one embodiment, human Tau antibody-based molecules of the present invention are generated in the HCo7 mouse model. HCo7 mice have a JKD disruption in their endogenous light chain (kappa) genes (as described in Chen et al., "B Cell Development In Mice That Lack One Or Both Immunoglobulin Kappa Light Chain Genes," *EMBO J.* 12:821-830 (1993), which is hereby incorporated by reference in its entirety), a CMD disruption in their endogenous heavy chain genes (as described in WO 01/14424, which is hereby incorporated by reference in its entirety), a KCo5 human kappa light chain transgene (as described in Fishwild, D. et al., "High-Avidity Human IgG Kappa Monoclonal Antibodies From A Novel Strain Of Minilocus Transgenic Mice," *Nature Biotechnol.* 14:845-851 (1996), which is hereby incorporated by reference in its entirety), and/or a HCo7 human heavy chain transgene (as described in U.S. Pat. No. 5,770,429, which is hereby incorporated by reference in its entirety).

In another embodiment, human Tau antibody-based molecules of the present invention are generated in the HCol2 mouse model. The HCol2 mice have a JKD disruption in their endogenous light chain (kappa) genes (as described in Chen et al., "B Cell Development In Mice That Lack One Or Both Immunoglobulin Kappa Light Chain Genes," *EMBO J.* 12:821-830 (1993), which is hereby incorporated by reference in its entirety), a CMD disruption in their endogenous heavy chain genes (as described in PCT Publication WO 01/14424, which is hereby incorporated by reference in its entirety), a KCo5 human kappa light chain transgene (as described in Fishwild, D. et al., "High-Avidity Human IgG Kappa Monoclonal Antibodies From A Novel Strain Of Minilocus Transgenic Mice," *Nature Biotechnol.* 14:845-851 (1996), which is hereby incorporated by reference in its entirety), and/or a HCol2 human heavy chain transgene (as described PCT Publication WO 01/14424, which is hereby incorporated by reference in its entirety).

In another embodiment, human Tau antibody-based molecules of the present invention are generated in the KM mouse model. In the KM mouse strain, the endogenous mouse kappa light chain gene has been homozygously disrupted as described in Chen et al., "B Cell Development In Mice That Lack One Or Both Immunoglobulin Kappa Light Chain Genes," *EMBO J.* 12:821-830 (1993), which is hereby incorporated by reference in its entirety) and the endogenous mouse heavy chain gene has been homozygously disrupted as described in PCT Publication WO 01/09187, which is hereby incorporated by reference in its entirety. This mouse strain carries a human kappa light chain transgene, KCo5, as described in Fishwild, D. et al., "High-Avidity Human IgG Kappa Monoclonal Antibodies From A Novel Strain Of Minilocus Transgenic Mice," *Nature Biotechnol.* 14:845-851 (1996), which is hereby incorporated by reference in its entirety). This mouse strain also carries a human heavy chain transchromosome composed of chromosome 14 fragment hCF (SC20) as described in PCT Publication WO 02/43478, which is hereby incorporated by reference in its entirety.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690; 5,756,687; 5,750,172 and 5,741,957, which are hereby incorporated by reference in their entirety.

In some antibodies only part of a CDR, namely the subset of CDR residues required for binding termed the "specificity determining residues" ("SDRs"), are needed to retain binding in a humanized antibody. CDR residues not contacting antigen and not in the SDRs can be identified based on previous studies from regions of Kabat CDRs lying outside Chothia hypervariable loops (see, Kabat et al., SEQUENCES OF PROTEINS OF IMMUNOLOGICAL INTEREST, National Institutes of Health Publication No. 91-3242 (1992); Chothia, C. et al., "Canonical Structures For The Hypervariable Regions Of Immunoglobulins," *J. Mol. Biol.* 196:901-917 (1987), which are hereby incorporated by reference in their entirety), by molecular modeling and/or empirically, or as described in Gonzales, N. R. et al., "SDR Grafting Of A Murine Antibody Using Multiple Human Germline Templates To Minimize Its Immunogenicity," *Mol. Immunol.* 41:863-872 (2004), which is hereby incorporated by reference in its entirety. In such humanized antibodies, at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The fact that a single amino acid alteration of a CDR residue can result in loss of functional binding or an enhancement of functional binding (Rudikoff, S. et al., "Single Amino Acid Substitution Altering Antigen-Binding Specificity," *Proc. Natl. Acad. Sci. USA* 79 (6): 1979-1983 (1982), which is hereby incorporated by reference in its entirety) provides a means for systematically identifying alternative functional CDR sequences. In one method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original CDR sequence to the identity of the substituted variant CDR sequence, the BLOSUM62.iij substitution score for that substitution can be identified. The BLOSUM system provides a matrix of amino acid substitutions created by analyzing a database of sequences for trusted alignments (Eddy, S.R., "Where Did The BLOSUM62 Alignment Score Matrix Come From?," *Nature Biotech.* 22 (8): 1035-1036 (2004); Henikoff, J. G., "Amino acid substitution matrices from protein blocks," *Proc. Natl. Acad. Sci. USA* 89:10915-10919 (1992); Karlin, S. et al., "Methods For Assessing The Statistical Significance Of Molecular Sequence Features By Using General Scoring Schemes," *Proc. Natl. Acad. Sci. USA* 87:2264-2268 (1990); Altschul, S.F., "Amino Acid Substitution Matrices From An Information Theoretic Perspective," *J. Mol. Biol.* 219, 555-565 (1991), which are hereby incorporated by reference in their entirety). Table 1 presents the BLOSUM62.iij substitution scores (the higher the score the more conservative the substitution and thus the more likely the substitution will not affect function). If an antibody-based molecule comprising the resultant CDR fails to bind to Tau, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

The present invention thus contemplates one or more conservative amino acid residue substitutions in one or more CDR sequences (i.e., SEQ TD NOs: 2-7) of the Tau antibody based molecule using guided or random mutagenesis to identify improved CDRs. In the context of the present invention, conservative substitutions may be defined by substitutions within the classes of amino acids reflected in one or more of the following three tables:

Amino Acid Residue Classes For Conservative Substitutions:

TABLE 2

| | |
|---|---|
| Acidic Residues | Asp (D) and Glu (E) |
| Basic Residues | Lys (K), Arg (R), and His (H) |

TABLE 2-continued

| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues:

TABLE 4

| Alcohol Group-Containing Residues | S and T |
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) PROTEINS: STRUCTURE AND MOLECULAR PROPERTIES (2d Ed. 1993), W. H. Freeman and Company, which is hereby incorporated by reference in its entirety.

Phage display technology can alternatively be used to increase (or decrease) CDR affinity of the antibody-based molecules of the present invention. This technology, referred to as affinity maturation, employs mutagenesis or "CDR walking" and re-selection using the target antigen or an antigenic fragment thereof to identify antibodies having CDRs that bind with higher (or lower) affinity to the antigen when compared with the initial or parental antibody (see, e.g. Glaser et al., "Antibody Engineering By Codon-Based Mutagenesis In A Filamentous Phage Vector System," *J. Immunology* 149:3903-3913 (1992), which is hereby incorporated by reference in its entirety). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify variant antibody-based binding molecules with increased or decreased affinity to the antigen (e.g., ELISA) (See Wu, H. et al., "Stepwise In Vitro Affinity Maturation Of Vitaxin, An Alphav Beta3-Specific Humanized mAb," *Proc. Natd. Acad. Sci. USA* 95:6037-6042 (1998); Yelton et al., "Affinity Maturation Of The BR96 Anti-Carcinoma Antibody By Codon-Based Mutagenesis," *J. Immunology* 155:1994 (1995), which are hereby incorporated by reference in their entirety). CDR walking, which randomizes the light chain, may be used (see, Schier, R. et al., "Isolation Of Picomolar Affinity Anti-c-erbB-2 Single-Chain Fv By Molecular Evolution Of The Complementarity Determining Regions In The Center Of The Antibody Binding Site," *J. Mol. Biol.* 263:551-567 (1996), which is hereby incorporated by reference in its entirety).

Methods for accomplishing such affinity maturation that are suitable for affinity maturation of the anti-Tau antibody molecule disclosed herein are described, for example, in Krause, J. C. et al., "An Insertion Mutation That Distorts Antibody Binding Site Architecture Enhances Function of a Human Antibody," *MBio.* 2(1): e00345-10 (2011); Kuan, C. T. et al., "Affinity-Matured Anti-Glycoprotein NMB Recombinant Immunotoxins Targeting Malignant Gliomas And Melanomas," *Int. J. Cancer* 10.1002/ijc.25645 (2010); Hackel, B. J. et al., "Stability And CDR Composition Biases Enrich Binder Functionality Landscapes," *J. Mol. Biol.* 401(1):84-96 (2010); Montgomery, D. L. et al., "Affinity Maturation And Characterization Of A Human Monoclonal Antibody Against HIV-1 gp41," *MAbs* 1(5):462-474 (2009); Gustchina, E. et al., "Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth," *Virology* 393(1):112-119 (2009); Finlay, W. J. et al., "Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions," *J. Mol. Biol.* 388(3):541-558 (2009); Bostrom, J. et al., "Improving Antibody Binding Affinity And Specificity For Therapeutic Development," *Methods Mol. Biol.* 525:353-376 (2009); Steidl, S. et al., "In Vitro Affinity Maturation Of Human GM-CSF Antibodies By Targeted CDR-Diversification," *Mol. Immunol.* 46(1): 135-144 (2008); and Barderas, R. et al., "Affinity Maturation Of Antibodies Assisted By In Silico Modeling," *Proc. Natd. Acad. Sci. USA* 105(26):9029-9034 (2008), which are hereby incorporated by reference in their entirety.

In one embodiment, the Tau-antibody based molecule as described herein comprise the amino acid sequence of any one, any two, any three, any four, any five, or any six CDRs as described herein. In one embodiment, the antibody-based molecule of the present invention comprises, alone or in combination with any of the other CDRs described herein, a heavy chain CDR1 (H-CDR1) comprising the amino acid sequence of SEQ ID NO: 2 (SYVIH), or a modified amino acid sequence of SEQ ID NO: 2, said modified sequence containing 1 or 2 amino acid residue modifications as compared to SEQ ID NO: 2. In one embodiment, the antibody-based molecule of the present invention comprises, alone or in combination with any of the other CDRs described herein, a heavy chain CDR2 (H-CDR2) comprising an amino acid sequence of SEQ ID NO: 3 (YIYPYNDGTIYNEKFKG), or a modified amino acid sequence of SEQ ID NO: 3, said modified sequence containing 1, 2, or 3 amino acid residue modifications as compared to SEQ ID NO: 3. In one embodiment, the antibody-based molecule of the present invention comprises, alone or in combination with any of the other CDRs described herein, a heavy chain CDR 3 (H-CDR3) comprising an amino acid sequence of SEQ ID NO: 4 (ERDNYGVY), or a modified amino acid sequence of SEQ ID NO: 4, said modified sequence containing 1 or 2 amino acid residue modifications as compared to SEQ ID NO: 4. In one embodiment, the antibody-based molecule of the present invention comprises, alone or in combination with any of the other CDRs described herein, a light chain CDR1 (L-CDR1) having an amino acid sequence of SEQ ID NO: 5 (RSSQSIVHSNGNTYLE), or a modified amino acid sequence of SEQ ID NO: 5, said modified sequence containing 1, 2, or 3 amino acid residue modifications as compared to SEQ ID NO: 5. In one embodiment, the antibody-based molecule of the present invention comprises, alone or in combination with any of the other CDRs described herein, a light chain CDR2 (L-CDR2) having an amino acid sequence of SEQ ID NO: 6 (KVSNRFY), or a modified amino acid sequence of SEQ ID NO: 6, said modified sequence containing 1 or 2 amino acid residue modifications as compared to SEQ ID NO: 6. In one embodiment, the antibody-based molecule of the present invention comprises, alone or in combination with any of the other CDRs described herein, a light chain CDR3 (L-CDR3) having an amino acid sequence of SEQ ID NO: 7 (FQDSHIPYT), or a modified amino acid sequence of SEQ ID NO: 7, said modified sequence containing 1 or 2 amino acid residue modifications as compared to SEQ ID NO: 7.

In one embodiment, the antibody-based molecule of the present invention comprises a $V_H$ domain, where the $V_H$ domain comprises the H-CDR1 having the amino acid sequence of SEQ ID NO: 2, or a modified amino acid sequence of SEQ ID NO: 2, said modified sequence containing 1 or 2 amino acid residue modifications as compared SEQ ID NO: 2; the H-CDR2 having the amino acid sequence of SEQ ID NO: 3, or a modified amino acid sequence of SEQ ID NO: 3, said modified sequence containing 1, 2, or 3 amino acid residue modifications as compared to SEQ ID NO: 3; and the H-CDR3 having the amino acid sequence of SEQ ID NO: 4, or a modified amino acid sequence of SEQ ID NO: 4, said modified sequence containing 1 or 2 amino acid residue modifications as compared to SEQ ID NO: 4.

In one embodiment, the antibody-based molecule comprises a $V_L$ domain, where the $V_L$ region comprises the L-CDR1 having the amino acid sequence of SEQ ID NO: 5, or a modified amino acid sequence of SEQ ID NO: 5, said modified sequence containing 1, 2, or 3 amino acid residue modifications as compared to SEQ ID NO: 5; the L-CDR2 having the amino acid sequence of SEQ ID NO: 6, or a modified amino acid sequence of SEQ ID NO: 6, said modified sequence containing 1 or 2 amino acid residue modifications as compared to SEQ ID NO: 6; and the L-CDR3 having the amino acid sequence of SEQ ID NO: 7, or a modified amino acid sequence of SEQ ID NO: 7, said modified sequence containing 1 or 2 amino acid residue modifications as compared to SEQ ID NO: 7.

Suitable amino acid modifications to the heavy chain CDR sequences and/or the light chain CDR sequences of the Tau antibody-based molecule disclosed herein include, for example, conservative substitutions or functionally equivalent amino acid residue substitutions that result in variant CDR sequences having similar or enhanced binding characteristics to those of the CDR sequences disclosed herein as described above.

The amino acid sequences of the heavy chain variable region CDRs and/or the light chain variable region CDRs of the Tau antibody-based molecule described herein may further comprise one or more internal neutral amino acid insertions or deletions that do not alter Tau binding. In one embodiment, the H-CDR3 having an amino acid sequence of SEQ ID NO: 4, further contains one or more internal neutral amino acid insertions or deletions that do not alter Tau binding. In another embodiment, the L-CDR1, having an amino acid sequence of SEQ ID NO: 5, further contains one or more internal neutral amino acid insertions or deletions that do not alter Tau binding.

In one embodiment of the present disclosure, the anti-Tau antibody-based molecule comprises a heavy chain variable region with a H-CDR1 having the amino acid sequence of SEQ ID NO: 2; a H-CDR2 having the amino acid sequence of SEQ ID NO: 3; and a H-CDR3 having the amino acid sequence of SEQ ID NO: 4. An exemplary heavy chain variable region comprising the aforementioned CDR regions has the amino acid sequence of SEQ ID NO: 8 as shown below. The CDR regions of the variable heavy chain of SEQ ID NO: 8 are underlined and the flanking framework regions (i.e., FR1-FR4) are shown in bold.

(SEQ ID NO: 8)
MEWSWIFLILLSGTAGVHSEVQLQQSGPELVKPGASVKMSCKASGYTFT<u>SY VIH</u>WVKQKPGQGLEWIG<u>YIYPYNDGTIYNEKFKG</u>KATLTSDTSSSTVYMEL ISLTAEDSAVYWCVR<u>ERDNYGVY</u>WGQGTTLTVSS

In one embodiment of the present disclosure, the anti-Tau antibody-based molecule comprises a light chain variable region with a L-CDR1 having the amino acid sequence of SEQ ID NO: 5, a L-CDR2 having the amino acid sequence of SEQ ID NO: 6, and a L-CDR3 having the amino acid sequence of SEQ ID NO: 7. An exemplary light chain variable region comprising the aforementioned CDR regions has the amino acid sequence of SEQ ID NO: 9 as shown below. The CDR regions of the variable light chain of SEQ ID NO: 9 are underlined and the framework regions (i.e., FR1-FR4) are shown in bold.

(SEQ ID NO: 9)
MKLPVRLLVLMFWIPASSSDVLLTQTPLSLPVSLGDQASISC<u>RSSQSIVHS NGNTYLE</u>WYLQKPGQSPELLIY<u>KVSNRFY</u>GVPDRFSGSGSGTDFTLKISRV EAEDLGVYYC<u>FQDSHIPYT</u>FGGGTRLEIK

In one embodiment, the anti-Tau antibody-based molecule as described herein comprises a heavy chain variable region having an amino acid sequence of SEQ ID NO: 8 and/or a light chain variable region having an amino acid sequence of SEQ ID NO:9. An exemplary anti-Tau antibody-based molecule of the present invention is the monoclonal antibody having the heavy chain variable region of SEQ ID NO: 8 and the light chain variable region of SEQ ID NO: 9, which is referred to herein as Tau mAb 8B2D1.

In another embodiment, the antibody-based molecule of the present invention comprises a heavy chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity with SEQ ID NO: 8, and/or a light chain variable region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity with SEQ ID NO: 9.

In one embodiment, the antibody-based molecule of the present disclosure comprises a humanized variant of the heavy chain variable region of SEQ ID NO: 8 and/or a humanized variant of the light chain variable region of SEQ ID NO: 9, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences within SEQ ID NOs: 8 and 9), or a combination of these approaches. The humanized framework regions are designed to be similar in length and sequence to the parental framework sequences of SEQ ID NO: 8 and SEQ ID NO: 9, respectively. In one embodiment, the humanized framework regions share 50%, 55%, 60%, 65%, 70%, 75%, 80%, 85%, 90%, 95% or more sequence identity to the framework regions of SEQ ID NO:8 and SEQ ID NO: 9, respectively. In another embodiment, the humanized framework regions are 60%, 65%, 70%, 75%, 80%, 85%, 90%, 95% or more similar in length to the framework regions of SEQ ID NO: 8 and SEQ ID NO: 9, respectively. Humanized variants of the heavy chain variable region of SEQ ID NO: 8 and the light chain variable region of SEQ ID NO:9 share at least 50%, at least 55%, at least 60%, at least 65%, at least 70%, at least 75%, at least 80%, at least 85%, at least 90%, at least 95% sequence identity along the entire length of SEQ ID NO: 8 and SEQ ID NO: 9, respectively.

In one embodiment of the present disclosure, the Tau antibody-based molecule is a scFv molecule. An exemplary Tau scFv of the present invention possess the same $V_L$ and $V_H$ domain CDRs as described infra for antibody 8B2D1.

An amino acid sequence of an exemplary Tau scFv is (SEQ ID NO: 18) (CDR residues are underlined):

MKLPVRLLVLMFWIPASSSDVLLTQTPLSLPVSLGDQASISCRSSQSIVHS

NGNTYLEWYLQKPGQSPELLIYKVSNRFYGVPDRFSGSGSGTDFTLKISRV

EAEDLGVYYCFQDSHIPYTFGGGTRLEIKssggggsggggggssrssME

WSWIFLILLSGTAGVHSEVQLQQSGPELVKPGASVKMSCKASGYTFTSYVI

-continued

HWVKQKPGQGLEWIGYIYPYNDGTIYNEKFKGKATLTSDTSSSTVYMELIS

LTAEDSAVYWCVRERDNYGVYWGQGTTLTVSS wherein amino acid residues 1-131 are the amino acid residues of the $V_L$ domain of SEQ ID NO:9, amino acid residues 132-149 are the amino acid residues of a linker (ssggggsggggggssrss SEQ ID NO: 19), and amino acid residues 150-285 are the amino acid residues of the $V_H$ domain of SEQ ID NO: 8.

In a preferred embodiment, an exemplary scFv is prepared as a fusion protein that includes an N-terminal leader peptide portion having the amino acid sequence of SEQ ID NO: 20 (IQEEFKMKKTAIAIAVALAGFATVAQAA), and/or a C-terminal peptide portion. The C-terminal peptide portion may include: an antibody constant domain having a sequence of SEQ ID NO: 21 (AKTTPPSVTSGQAGQ) (Hussein, A. H. et al., "Construction and Characterization of Single-Chain Variable Fragment Antibodies Directed against the *Bordetella pertussis* Surface Adhesins Filamentous Hemagglutinin and Pertactin," *Infect. Immun.* 75(11): 5476-5482 (2007), which is hereby incorporated by reference in its entirety), a His-Tag having the sequence of SEQ ID NO: 22 (HHIIIIIIIH), and/or an HA-Tag having the sequence of SEQ ID NO: 23 (GAYPYDVPDYAS), or any combination or sub-combination thereof, and in any order. A preferred C-terminal peptide portion has the amino acid sequence of SEQ ID NO: 24 (AKTTPPSVTSGQAGQHII-HIHHGAYPYDVPDYAS), and thus includes (in the N-terminus to C-Terminus direction) SEQ ID NO: 21, SEQ ID NO: 22, and SEQ ID NO: 23

Although scFv antibodies are able to transit across the blood-brain barrier, various ancillary approaches may be used to further promote such transit (Huang, L. et al., "Single-Chain Fragment Variable Passive Immunotherapies For Neurodegenerative Diseases," *Int. J. Mol. Sci.* 14(9): 19109-19127 (2013), which is hereby incorporated by reference in its entirety). A limited set of proteins and peptides are transported across the blood-brain barrier via receptor-mediated transcytosis (Herve, F. et al., "CNS Delivery Via Adsorptive Transcytosis," *AAPSJ.* 10(3):455-472 (2008), which is hereby incorporated by reference in its entirety), the three best-studied ligands being insulin, iron-transferrin and LDL-cholesterol (Bickel, U. et al., "Delivery Of Peptides And Proteins Through The Blood-Brain Barrier," *Adv. Drug Deliv. Rev.* 46:247-279 (2001); Tuma, P. L. et al., "Transcytosis: Crossing Cellular Barriers," *Physiol. Rev.* 83:871-932 (2003), which are hereby incorporated by reference in their entirety). Thus, transport of a scFv across the blood-brain barrier can be promoted by fusing the scFv to an antibody, or an epitope-binding fragment thereof, that is immunospecific for a receptor of such ligands (e.g., the human insulin receptor (HIR), the transferrin receptor (TfR), low density lipoprotein receptor-related proteins 1 (LRP1) and 2 (LRP2), non-toxic diphtheria toxin receptor/Heparin binding epidermal growth factor-like growth factor, etc.). The resulting fusion protein can be transported across the blood-brain barrier through its binding to the receptor (Boado, R. J. et al., "IgG-Single-Chain Fv Fusion Protein Therapeutic For Alzheimer's Disease: Expression In CHO cells And Pharmacokinetics And Brain Delivery In The Rhesus Monkey," *Biotechnol. Bioeng.* 105:627-635 (2010); Jones, A. R. et al., "Blood-Brain Barrier Transport Of Therapeutics Via Receptor-Mediation," *Pharm. Res.* 24(9):1759-1771 (2007); Wang, Y. Y. et al., "Receptor-Mediated Therapeutic Transport Across The Blood-Brain Barrier," *Immunotherapy* 1(6): 983-993 (2009); Lajoie, J. M. et al., "Targeting Receptor-Mediated Transport For Delivery Of Biologics Across The Blood-Brain Barrier," *Annu. Rev. Pharmacol. Toxicol.* 55:613-631 (2015); Pardridge, W. M., "Drug Transport Across The Blood-Brain Barrier," *J. Cereb. BloodFlow Metab.* 32(11):1959-1972 (2012); Bhaskar, S. et al., "Multifunctional Nanocarriers For Diagnostics, Drug Delivery And Targeted Treatment Across Blood-Brain Barrier: Perspectives On Tracking And Neuroimaging," *Part. Fibre. Toxicol.* 7:3 pp. 1-25 (2010), which are hereby incorporated by reference in their entirety).

The scFv may be augmented to contain a polycationic peptide that facilitates adsorptive-mediated transcytosis. Suitable polycationic peptides include hexamethylene-diamine, putrescine, spermidine and spermine (Herve, F. et al., "CNS Delivery Via Adsorptive Transcytosis," *AAPSJ.* 10(3):455-472 (2008); Kandimalla, K. K. et al., "Physiological And Biophysical Factors That Influence Alzheimer's Disease Amyloid Plaque Targeting Of Native And Putrescine Modified Human Amyloid Beta40," *J. Pharmacol. Exp. Ther.* 318:17-25 (2006), which are hereby incorporated by reference in their entirety). The scFv may be augmented to comprise polycationic groups via treatment that amidates some or all of its carboxylic groups (i.e., the carboxy-terminal group, or the carboxylic side chains of glutamate or aspartate residue(s) of the scFv).

Alternatively, the scFv may be augmented to contain a cell-penetrating peptide ("CPP") (Rao, K. S. et al., "Targeting Anti-HIV Drugs To The CNS," *Expert Opin. Drug Deliv.* 6(8):771-784 (2009); Mathupala, S. P. et al., "Delivery Of Small-Interfering RNA (siRNA) To The Brain," *Expert Opin. Ther. Pat.* 19(2):137-140 (2009); Herve, F. et al., "CNS Delivery Via Adsorptive Transcytosis," *AAPSJ.* 10(3):455-472) (2008), which are hereby incorporated by reference in their entirety). Such peptides include the HIV-1 trans-activating transcriptional activator (TAT) peptide, the Herpes Simplex Virus type-1 transcription factor (HSV VP-22) peptide, antennapedia and penetratin (Wadia, J. S. et al., "Transducible TAT-HA Fusogenic Peptide Enhances Escape Of TAT-Fusion Proteins After Lipid Raft Macropinocytosis," *Nat. Med.* 10:310-315 (2004); Richard, J. P. et al., "Cell-Penetrating Peptides. A Reevaluation Of The Mechanism Of Cellular Uptake," *J. Biol. Chem.* 278:585-590 (2003); Temsamani, J. et al., "The Use Of Cell-Penetrating Peptides For Drug Delivery," *Drug Discov. Today* 9:1012-1019 (2004), which are hereby incorporated by reference in their entirety).

Another aspect of the present disclosure is directed to an antibody mimetic that binds Tau protein. An "antibody mimetic" as referred to herein encompasses any organic compound, e.g., a peptide or polypeptide, that can specifically bind an antigen like an antibody, and is about 3-20 kDa. In one embodiment, the antibody mimetic comprises a scaffold which binds its antigen via amino acids in exposed loops similar to the CDR loops of an antibody. These antibody mimetics include, without limitation, adnectins, lipocalins, Kunitz domain-based binders, avimers, knottins, fynomers, atrimers, and cytotoxic T-lymphocyte associated protein-4 (CTLA4)-based binders (reviewed in Weidle et al., "The Emerging Role of New Protein Scaffold-based Agents for the Treatment of Cancer," *Cancer Genomics & Proteomics* 10:155-168 (2013), which is hereby incorporated by reference in its entirety). In accordance with this aspect of the present disclosure, the loop binding regions of the antibody mimetic are adapted to comprise one or more of the heavy chain and/or light chain CDRs of the antibodies disclosed herein. For example, an antibody mimetic of the present disclosure may comprise a first loop region having an amino acid sequence of SEQ ID NO: 2 or a modified amino acid sequence of SEQ ID NO: 2 said modified sequence containing 1 or 2 amino acid residue modifications as compared to SEQ ID NO: 2. The antibody mimetic may comprise another loop region having an amino acid sequence of SEQ ID NO: 3, or a modified amino acid sequence of SEQ ID NO: 3, said modified sequences containing 1, 2, or 3 amino acid residue modifications as compared to SEQ ID NO: 3. The antibody mimetic may comprise another loop region having an amino acid sequence of SEQ ID NO: 4, or a modified amino acid sequence of SEQ ID NO: 4, said modified sequence containing 1 or 2 amino acid residue modifications as compared to SEQ ID NO: 4. The antibody mimetic may further comprise another loop region having an amino acid sequence of SEQ ID NO: 5, or a modified amino acid sequence of SEQ ID NO: 5, said modified sequence containing 1, 2, or 3 amino acid residue modifications as compared to SEQ ID NO: 5. The antibody mimetic may comprise another loop region having an amino acid sequence of SEQ ID NO: 6, or a modified amino acid sequence of SEQ ID NO: 6, said modified sequence containing 1 or 2 amino acid residue modifications as compared to SEQ ID NO: 6. The antibody mimetic may comprise another loop region having an amino acid sequence of SEQ ID NO: 7, or a modified amino acid sequence of SEQ ID NO: 7, said modified sequence containing 1 or 2 amino acid residue modifications as compared to SEQ ID NO: 7.

In one embodiment, the antibody mimetic comprises one or more modified fibronectin type III (FN3) domains (e.g., an adnectin or centyrin molecule), where each modified FN3 domain has one or more loop regions that comprise one or more CDR sequences or modified CDR sequences as disclosed herein.

The FN3 domain is an evolutionary conserved protein domain that is about 100 amino acids in length and possesses a beta sandwich structure. The beta sandwich structure of human FN3 comprises seven beta-strands, referred to as strands A, B, C, D, E, F, G, with six connecting loops, referred to as loops AB, BC, CD, DE, EF, and FG that exhibit structural homology to immunoglobulin binding domains. Three of the six loops, i.e., loops DE, BC, and FG, correspond topologically to the complementarity determining regions of an antibody, i.e., CDR1, CDR2, and CDR3. The remaining three loops are surface exposed in a manner similar to antibody CDR3. In accordance with the present disclosure, one or more of the loop regions of each FN3 domain of the binding molecule are modified to comprise one or more CDR sequences disclosed herein.

The modified FN3 domain can be a FN3 domain derived from any of the wide variety of animal, yeast, plant, and bacterial extracellular proteins containing these domains. In one embodiment, the FN3 domain is derived from a mammalian FN3 domain. Exemplary FN3 domains include, for example and without limitation, any one of the 15 different FN3 domains present in human tenascin C, or the 15 different FN3 domains present in human fibronectin (FN) (e.g., the $10^{th}$ fibronectin type III domain). Exemplary FN3 domains also include non-natural synthetic FN3 domains, such as those described in U.S. Pat. Publ. No. 2010/0216708 to Jacobs et al., which is hereby incorporated by reference in its entirety. Individual FN3 domains are referred to by domain number and protein name, e.g., the $3^{rd}$ FN3 domain of tenascin (TN3), or the $10^{th}$ FN3 domain of fibronectin (FN10).

Another aspect of the present disclosure is directed to isolated polynucleotides encoding the Tau antibody-based molecule or antibody mimetic as described herein. In one embodiment, the polynucleotide encoding the Tau antibody of the present invention comprises a sequence encoding any one, any two, any three, any four, any five, or any six of the CDRs described supra. In one embodiment, the polynucleotide comprises the sequence of SEQ ID NO: 10 (AGC-TATGTTATTCAC) encoding the H-CDR1 of SEQ ID NO: 2. In one embodiment, the polynucleotide comprises the sequence of SEQ ID NO: 11 (TATATTTATCCTTACAAT-GATGGTACTATTTACAATGAGAAATTCAAAGGC) encoding the H-CDR2 of SEQ ID NO: 3. In one embodiment, the polynucleotide comprises the sequence of SEQ ID NO: 12 (GAGAGGGATAATTACGGGGTCTAT) encoding the H-CDR3 of SEQ ID NO: 4. In one embodiment, the polynucleotide comprises the sequence of SEQ ID NO: 13 (AGATCTAGTCAGAGCATTGTACATAGTAATG-GAAACACCTATTTAGAG) encoding the L-CDR1 of SEQ ID NO: 5. In one embodiment, the polynucleotide comprises the sequence of SEQ ID NO: 14 (AAAGTTTCCAACC-GATTTTAT) encoding the L-CDR2 of SEQ ID NO: 6. In one embodiment, the polynucleotide comprises the sequence of SEQ ID NO: 15 (TTTCAAGATTCACATATTCCGTA-CACG) encoding the L-CDR3 of SEQ ID NO: 7.

In one embodiment, the polynucleotide as described herein encodes a $V_H$ domain comprising the H-CDR1 having the amino acid sequence of SEQ ID NO: 2, or a modified amino acid sequence of SEQ ID NO: 2, said modified sequence containing 1 or 2 amino acid residue modifications as compared SEQ ID NO: 2; the H-CDR2 having the amino acid sequence of SEQ ID NO: 3, or a modified amino acid sequence of SEQ ID NO: 3, said modified sequence containing 1, 2, or 3 amino acid residue modifications as compared to SEQ ID NO: 3; and the H-CDR3 having the amino acid sequence of SEQ ID NO: 4, or a modified amino acid sequence of SEQ ID NO: 4, said modified sequence containing 1 or 2 amino acid residue modifications as compared to SEQ ID NO: 4. An exemplary polynucleotide encoding a $V_H$ domain of the Tau antibody-based molecule as described herein (SEQ ID NO: 8) comprises the nucleotide sequence of SEQ ID NO: 16 as shown below. The portions of the sequence encoding the $V_H$ CDRs are underlined.

(SEQ ID NO: 16)
ATGGAATGGAGTTGGATATTTCTCATTCTCCTGTCAGGAACTGCAGGTGT

CCACTCTGAGGTCCAGCTGCAACAGTCTGGACCTGAGCTGGTAAAGCCTG

GGGCTTCCGTGAAGATGTCCTGCAAGGCTTCTGGATACACATTCACT<u>AGC</u>

<u>TATGTTATTCAC</u>TGGGTGAAGCAGAAGCCTGGGCAGGGCCTTGAGTGGAT

TGGA<u>TATATTTATCCTTACAATGATGGTACTATTTACAATGAGAAATTCA</u>

<u>AAGGC</u>AAGGCCACACTGACTTCAGACACATCCTCCAGCACAGTCTACATG

GAACTCATCAGCCTGACCGCTGAGGACTCTGCGGTCTATTGGTGTGTAAG

A<u>GAGAGGGATAATTACGGGGTCTAT</u>TGGGGCCAAGGCACCACTCTCACAG

TCTCCTCA

In one embodiment, the polynucleotide as described herein encodes a $V_L$ region comprising the L-CDR1 having the amino acid sequence of SEQ ID NO: 5, or a modified amino acid sequence of SEQ ID NO: 5, said modified sequence containing 1, 2, or 3 amino acid residue modifications as compared to SEQ ID NO: 5; the L-CDR2 having the amino acid sequence of SEQ ID NO: 6, or a modified amino acid sequence of SEQ ID NO: 6, said modified sequence containing 1 or 2 amino acid residue modifications as compared to SEQ ID NO: 6; and the L-CDR3 having the amino acid sequence of SEQ ID NO: 7, or a modified amino acid sequence of SEQ ID NO: 7, said modified sequence containing 1 or 2 amino acid residue modifications as compared to SEQ ID NO: 7. An exemplary polynucleotide encoding a $V_L$ domain of the Tau antibody-based molecule as described herein (i.e., SEQ ID NO: 9) comprises the nucleotide sequence of SEQ ID NO: 17 as shown below. The portions of the sequence encoding the $V_L$ CDRs are underlined.

SEQ ID NO: 17)
ATGAAGTTGCCTGTTAGGCTGTTGGTGCTGATGTTCTGGATTCCTGCTTC

CAGCAGTGATGTTTTGCTGACCCAAACTCCACTCTCCCTGCCTGTCAGTC

TTGGAGATCAAGCCTCCATCTCTTGC<u>AGATCTAGTCAGAGCATTGTACAT</u>

<u>AGTAATGGAAACACCTATTTAGAG</u>TGGTACCTGCAGAAACCAGGCCAGTC

TCCAGAGCTCCTGATCTAC<u>AAAGTTTCCAACCGATTTTAT</u>GGGGTCCCAG

ACAGGTTCAGTGGCAGTGGATCAGGGACAGATTTCACACTCAAGATCAGC

AGAGTGGAGGCTGAGGATCTGGGAGTTTATTACTGC<u>TTTCAAGATTCACA</u>

<u>TATTCCGTACACGTT</u>CGGAGGGGGGACCAGGTTGGAAATAAAA

In one embodiment, the isolated polynucleotide encoding the anti-Tau antibody based molecule encodes the $V_H$ domain having the amino acid sequence of SEQ ID NO: 8. An exemplary polynucleotide encoding the $V_H$ of SEQ ID NO: 8 has a nucleotide sequence of SEQ ID NO: 16. In another embodiment, the isolated polynucleotide encodes the $V_L$ domain having the amino acid sequence of SEQ ID NO: 9. An exemplary polynucleotide encoding the $V_L$ of SEQ ID NO: 9 has a nucleotide sequence of SEQ ID NO: 17. In another embodiment, the isolated polynucleotide encoding the anti-Tau antibody based molecule encodes the $V_H$ domain having the amino acid sequence of SEQ ID NO: 8 and the $V_L$ domain having the amino acid sequence of SEQ ID NO: 9. The nucleic acid molecules described herein include isolated polynucleotides, portions of expression vectors or portions of linear DNA sequences, including linear DNA sequences used for in vitro transcription/translation, and vectors compatible with prokaryotic, eukaryotic or filamentous phage expression, secretion, and/or display of the antibodies or binding fragments thereof described herein.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding for example a linker sequence, a marker or a tag sequence, such as a histidine tag or an HA tag to facilitate purification or detection of the protein, a signal sequence, a fusion protein partner such as RepA, Fc portion, or bacteriophage coat protein such as pIX or pIII.

Another embodiment of the disclosure is directed to a vector comprising at least one polynucleotide encoding the Tau antibody-based molecule or antibody mimetic as described herein. Such vectors include, without limitation, plasmid vectors, viral vectors, including without limitation, vaccina vector, lentiviral vector, adenoviral vector, adeno-associated viral vector, vectors for baculovirus expression, transposon based vectors or any other vector suitable for introduction of the polynucleotides described herein into a given organism or genetic background by any means to facilitate expression of the encoded antibody polypeptide. In one embodiment, the polynucleotide sequence encoding the heavy chain variable domain, alone or together with the polynucleotide sequence encoding the light chain variable domain as described herein, are combined with sequences of a promoter, a translation initiation segment (e.g., a ribosomal binding sequence and start codon), a 3' untranslated region, polyadenylation signal, a termination codon, and transcription termination to form one or more expression vector constructs.

In one embodiment, the vector is an adenoviral-associated viral (AAV) vector. A number of therapeutic AAV vectors suitable for delivery of the polynucleotides encoding tau antibodies described herein to the central nervous system are known in the art. See e.g., Deverman et al., "Gene Therapy for Neurological Disorders: Progress and Prospects," *Nature Rev.* 17:641-659 (2018), which in hereby incorporated by reference in its entirety. Suitable AAV vectors include serotypes AAV1, AAV2, AAV3, AAV4, AAV5, AAV6, AAV7, AAV8, AAV9, AAV10, or AAV 11 in their native form or engineered for enhanced tropism. AAV vectors known to have tropism for the CNS that are particularly suited for therapeutic expression of the tau antibodies described herein include, AAV1, AAV2, AAV4, AAV5, AAV8 and AAV9 in their native form or engineered for enhanced tropism. In one embodiment, the AAV vector is an AAV2 vector. In another embodiment, the AAV vector is an AAV5 vector as described by Vitale et al., "Anti-tau Conformational scFv MC1 Antibody Efficiently Reduces Pathological Tau Species in Adult JNPL3 Mice," *Acta Neuropathol. Commun.* 6:82 (2018), optionally containing the GFAP or CAG promoter and the Woodchuck hepatitis virus (WPRE) post-translational regulatory element. In another embodiment, the AAV vector is an AAV9 vector as described by Haiyan et al., "Targeting Root Cause by Systemic scAAV9-hIDS Gene Delivery: Functional Correction and Reversal of Severe MPSII in Mice," *Mol. Ther. Methods Clin. Dev.* 10:327-340 (2018), which is hereby incorporated by reference in its entirety. In another embodiment, the AAV vector is an AAVrh10 vector as described by Liu et al., "Vectored Intracerebral Immunizations with the Anti-Tau Monoclonal Antibody PHF1 Markedly Reduces Tau Pathology in Mutant Transgenic Mice," *J. Neurosci.* 36(49): 12425-35 (2016), which is hereby incorporated by reference in its entirety.

In another embodiment the AAV vector is a hybrid vector comprising the genome of one serotype, e.g., AAV2, and the capsid protein of another serotype, e.g., AAV1 or AAV3-9 to control tropism. See e.g., Broekman et al., "Adeno-associated Virus Vectors Serotyped with AAV8 Capsid are More Efficient than AAV-1 or -2 Serotypes for Widespread Gene Delivery to the Neonatal Mouse Brain," *Neuroscience* 138: 501-510 (2006), which is hereby incorporated by reference in its entirety. In one embodiment, the AAV vector is an AAV2/8 hybrid vector as described by Ising et al., "AAV-mediated Expression of Anti-Tau ScFv Decreases Tau Accumulation in a Mouse Model of Tauopathy," *J. Exp. Med.* 214(5):1227 (2017), which is hereby incorporated by reference in its entirety. In another embodiment the AAV vector is an AAV2/9 hybrid vector as described by Simon et al., "A Rapid Gene Delivery-Based Mouse Model for Early-Stage Alzheimer Disease-Type Tauopathy," *J. Neuropath. Exp. Neurol.* 72(11): 1062-71 (2013), which is hereby incorporated by reference in its entirety.

In another embodiment, the AAV vector is one that has been engineered or selected for its enhanced CNS transduction after intraparenchymal administration, e.g., AAV-DJ (Grimm et al., *J. Viol.* 82:5887-5911 (2008), which is hereby incorporated by reference in its entirety); increased transduction of neural stem and progenitor cells, e.g., SCH9 and AAV4.18 (Murlidharan et al., *J. Virol.* 89: 3976-3987 (2015) and Ojala et al., *Mol. Ther.* 26:304-319 (2018), which are hereby incorporated by reference in their entirety); enhanced retrograde transduction, e.g., rAAV2-retro (Muller et al., *Nat. Biotechnol.* 21:1040-1046 (2003), which is hereby incorporated by reference in its entirety); selective transduction into brain endothelial cells, e.g., AAV-BRI (Korbelin et al., *EMBO Mol. Med.* 8: 609-625 (2016), which is hereby incorporated by reference in its entirety); or enhanced transduction of the adult CNS after IV administration, e.g., AAV-PHP.B and AAVPHP.eB (Deverman et al., *Nat. Biotechnol.* 34: 204-209 (2016) and Chan et al., *Nat. Neurosci.* 20: 1172-1179 (2017), which are hereby incorporated by reference in their entirety.

In accordance with this embodiment, the expression vector construct encoding the Tau antibody-based molecule can include the polynucleotide sequence encoding the heavy chain polypeptide, a fragment thereof, a variant thereof, or combinations thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region. In some embodiments, the heavy chain polypeptide can include a VH region and a CH1 region. In other embodiments, the heavy chain polypeptide includes a VH region, a CH1 region, a hinge region, a CH2 region, and a CH3 region.

The expression construct can also include a nucleic acid sequence encoding the light chain polypeptide, a fragment thereof, a variant thereof, or combinations thereof. The light chain polypeptide can include a variable light chain (VL) region and/or a constant light chain (CL) region.

The expression construct also typically comprises a promoter sequence suitable for driving expression of the Tau antibody-based molecule. Suitable promoter sequences include, without limitation, the elongation factor 1-alpha promoter (EFla) promoter, a phosphoglycerate kinase-1 promoter (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter. Other promoters suitable for driving gene expression in mammalian cells that are known in the art are also suitable for incorporation into the expression constructs disclosed herein.

The expression construct can further encode a linker sequence. The linker sequence can encode an amino acid sequence that spatially separates and/or links the one or more components of the expression construct (heavy chain and light chain components of the encoded antibody).

Another embodiment of the invention is a host cell comprising the vectors described herein. The Tau antibody-based molecule described herein can be optionally produced by a cell line, a mixed cell line, an immortalized cell or clonal population of immortalized cells, as well known in the art (see e.g., Ausubel et al., ed., Current Protocols in Molecular Biology, John Wiley & Sons, Inc., NY, N.Y. (1987-2001); Sambrook et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan et al., eds., Current Protocols in Immunology, John Wiley & Sons, Inc., NY (1994-2001); Colligan et al., Current Protocols in Protein Science, John Wiley & Sons, NY, N.Y., (1997-2001), which are hereby incorporated by reference in their entirety).

In some embodiments, the host cell chosen for expression may be of mammalian origin. Suitable mammalian host cells include, without limitation, COS-1 cells, COS-7 cells, HEK293 cells, BHK21 cells, CHO cells, BSC-1 cells, HeG2 cells, SP2/0 cells, HeLa cells, mammalian myeloma cells, mammalian lymphoma cells, or any derivative, immortalized or transformed cell thereof. Other suitable host cells include, without limitation, yeast cells, insect cells, and plant cells. Alternatively, the host cell may be selected from a species or organism incapable of glycosylating polypeptides, e.g., a prokaryotic cell or organism, such as BL21, BL21(DE3), BL21-GOLD(DE3), XL1-Blue, JM109, HMS174, HMS174(DE3), and any of the natural or engineered E. coli spp, Klebsiella spp., or Pseudomonas spp strains.

The Tau antibody-based molecules described herein can be prepared by any of a variety of techniques using the isolated polynucleotides, vectors, and host cells described supra. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. Standard molecular biology techniques are used to prepare the recombinant expression vector, transfect the host cells, select for transformants, culture the host cells and recover the antibody from the culture medium. Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like. Although it is possible to express the antibodies described herein in either prokaryotic or eukaryotic host cells, expression of antibodies in eukaryotic cells is sometimes preferable, and sometimes preferable in mammalian host cells, because such eukaryotic cells (and in particular mammalian cells) are more likely than prokaryotic cells to assemble and secrete a properly folded and immunologically active antibody.

As noted above, exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA,* 77: 4216-4220 (1980), which is hereby incorporated by reference in its entirety). Other suitable mammalian host cells include, without limitation, NSO myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown.

Host cells can also be used to produce functional antibody fragments, such as Fab fragments or scFv molecules. It is understood that variations on the above procedure are within the scope of the present disclosure. For example, it may be desirable to transfect a host cell with DNA encoding functional fragments of either the light chain and/or the heavy chain of an antibody described herein. Recombinant DNA technology may also be used to remove some or all of the DNA encoding either or both of the light and heavy chains that is not necessary for binding to the antigens of interest. The molecules expressed from such truncated DNA molecules are also encompassed by the antibodies described herein.

The antibodies and antibody binding fragments are recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Pharmaceutical Compositions of the Present Invention

The Tau antibody-based molecules or polynucleotide encoding the Tau antibody-based molecules of the present invention are advantageously administered as pharmaceutical compositions comprising an active therapeutic agent and one or more of a variety of other pharmaceutically acceptable components. See REMINGTON: THE SCIENCE AND PRACTICE OF PHARMACY ($21^{st}$ Edition) (2005) (Troy, D. B. et al. (Eds.) Lippincott Williams & Wilkins (Publs.), Baltimore Md.), which is hereby incorporated by reference in its entirety. The preferred form depends on the intended mode of administration and therapeutic application. The compositions can also include, depending on the formulation desired, pharmaceutically acceptable, non-toxic carriers, excipients, diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition, and which are vehicles commonly used to formulate pharmaceutical compositions for animal or human administration. The diluent is selected to not affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. Examples of suitable aqueous and non-aqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well-known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Suitability for carriers and other components of pharmaceutical compositions is determined based on the lack of significant negative impact on the desired biological properties of the active antibody-based molecule of the present invention (e.g., less than a substantial impact (e.g., 10% or less relative inhibition, 5% or less relative inhibition, etc.) on antigen binding).

The pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well-known in the art. Methods for the preparation of such formulations are generally known to those skilled in the art. See, e.g., SUSTAINED AND CONTROLLED RELEASE DRUG DELIVERY SYSTEMS, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art.

Pharmaceutical compositions for injection must typically be sterile and stable under the conditions of manufacture and storage. The composition may be formulated as a solution, microemulsion, liposome, or other ordered structure suitable to achieve high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

For parenteral administration, agents of the present invention are typically formulated as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions. Agents of the invention can be administered in the form of a depot injection or implant preparation which can be formulated in such a manner as to permit a sustained release of the active ingredient. An exemplary composition comprises an scFv at about 5 mg/mL, formulated in aqueous buffer consisting of 50 mM L-histidine, 150 mM NaCl, adjusted to pH 6.0 with HCl.

Typically, compositions are thus prepared as injectables, either as liquid solutions or suspensions; solid forms suitable for solution in, or suspension in, liquid vehicles prior to injection can also be prepared. The preparation also can be emulsified or encapsulated in liposomes or micro particles, such as polylactide, polyglycolide, or copolymer, for enhanced adjuvant effect (Langer, et al., Science 249:1527 (1990); Hanes, et al., Advanced Drug Delivery Reviews 28:97-119 (1997), which are hereby incorporated by reference in their entirety). Additional formulations suitable for other modes of administration include oral, intranasal, and pulmonary formulations, suppositories, and transdermal applications.

Administration of the Pharmaceutical Compositions of the Present Invention

The molecules of the present invention can be administered by parenteral, topical, oral or intranasal means for prophylactic and/or therapeutic treatment. Intramuscular injection (for example, into the arm or leg muscles) and intravenous infusion are preferred methods of administration of the molecules of the present invention. In some methods, such molecules are administered as a sustained release composition or device, such as a Medipad™ device (Elan Pharm. Technologies, Dublin, Ireland). In some methods, the molecules of the present invention are injected directly into a particular tissue where deposits have accumulated, for example intracranial injection.

In one embodiment, a pharmaceutical composition of the present invention is administered parenterally. The phrases "parenteral administration" and "administered parenterally" as used herein denote modes of administration other than enteral and topical administration, usually by injection, and include epidermal, intravenous, intramuscular, intraarterial, intrathecal, intracapsular, intracranial, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection, subcutaneous and infusion. In one embodiment that pharmaceutical composition is administered by intravenous or subcutaneous injection or infusion.

In prophylactic applications, pharmaceutical compositions or medicaments are administered to a patient susceptible to, or otherwise at risk of, Alzheimer's disease or other Tauopathy in an amount sufficient to eliminate or reduce the risk, lessen the severity, or delay the outset of the disease, including biochemical, histologic and/or behavioral symptoms of the disease, its complications and intermediate pathological phenotypes presented during development of the disease.

In therapeutic applications (i.e., in applications involving a patient who has been diagnosed as having Alzheimer's disease or other Tauopathy) the therapeutic molecules of the present invention are administered to such patient in an amount sufficient to cure, treat, or at least partially arrest, the symptoms of the disease (as adduced by biochemical, histologic and/or behavioral assessment), including its complications and intermediate pathological phenotypes in development of the disease. In some embodiments, the administration of the therapeutic molecules of the present invention reduces or eliminates mild cognitive impairment in patients that have not yet developed characteristic Alzheimer's pathology.

Effective doses of the provided therapeutic molecules of the present invention, for the treatment of the above-described conditions may vary depending upon many different factors, including means of administration, target site, physiological state of the patient, other medications administered, and whether treatment is prophylactic or therapeutic. Treatment dosages are typically titrated to optimize their safety and efficacy. On any given day that a dosage is given, the dosage of the Tau antibody-based molecule as described herein may range from about 0.0001 to about 100 mg/kg, and more usually from about 0.01 to about 5 mg/kg, of the patient's body weight. For example, dosages can be 1 mg/kg body weight or 10 mg/kg body weight or within the range of 1-10 mg/kg body weight. Exemplary dosages thus include: from about 0.1 to about 10 mg/kg body weight, from about 0.1 to about 5 mg/kg body weight, from about 0.1 to about 2 mg/kg body weight, from about 0.1 to about 1 mg/kg body weight, for instance about 0.15 mg/kg body weight, about 0.2 mg/kg body weight, about 0.5 mg/kg body weight, about 1 mg/kg body weight, about 1.5 mg/kg body weight, about 2 mg/kg body weight, about 5 mg/kg body weight, or about 10 mg/kg body weight A physician or veterinarian having ordinary skill in the art may readily determine and prescribe the effective amount of the pharmaceutical composition required. For example, the physician or veterinarian could start doses of antibody-based molecule in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible the antibody-based molecule of the present invention to be administered alone, it is preferable to administer the antibody-based molecule as a pharmaceutical composition as described above.

The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered such therapeutic molecule using a prophylactic dosage regime.

For therapeutic purposes, the Tau antibody-based molecules of the present invention are usually administered on multiple occasions. Intervals between single dosages (e.g., a bolus or infusion) can be weekly, monthly, or yearly. In some methods, dosage is adjusted to achieve a plasma concentration of 1-1000 µg/mL and in some methods 25-300 µg/mL. Alternatively, the therapeutic molecules of the present invention can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and non-human antibodies. scFv molecules generally have short serum half-lives.

Another aspect of the present invention is a combination therapy wherein a second antibody-based molecule recognizing the Tau protein is administered in combination with the antibody-based molecule of the present invention. In the case of amyloidogenic diseases such as, Alzheimer's disease and Down's syndrome, immune modulation to clear amyloid-beta (Aβ) deposits is an emerging therapy. Immunotherapies targeting Aβ have consistently resulted in cognitive improvements. It is likely that Tau and Aβ pathologies are synergistic. Therefore, a combination therapy targeting the clearance of both pathologies at the same time may be more effective than targeting each individually. In the case of Parkinson's Disease and related neurodegenerative diseases, immune modulation to clear aggregated forms of the α-synuclein protein is also an emerging therapy. A combination therapy which targets the clearance of both Tau and α-synuclein proteins simultaneously may be more effective than targeting each individually.

In another embodiment, a pharmaceutical composition comprising a recombinant nucleic acid sequence encoding the Tau antibody-based molecule as described herein, is administered to a subject to facilitate in vivo expression and formation of the antibody-based molecule for the treatment or prevention of conditions mediated by Tau accumulation or pathological forms of Tau. Expression vector constructs suitable for use in this embodiment of the disclosure are described supra.

The polynucleotide compositions can result in the generation of the Tau antibody-based molecule in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the antibody-based molecule in the subject within at least about 1 day, 2 days, 3 days, 4 days, 5 days, 6 days, 7 days, 8 days, 9 days, or 10 days of administration of the composition to the subject. The composition can result in generation of the antibody-based molecule in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the persistent generation of the antibody-based molecule in the subject. The composition can result in the generation of the antibody-based molecule in the subject for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

Diagnostic Utility of the Tau-Binding Antibody-Based Molecules

Detecting the presence of a pathological Tau conformer in a subject using the antibody-based molecule of the present invention can be achieved by obtaining a biological sample from the subject (e.g., blood, urine, cerebral spinal fluid), contacting the biological sample with said antibody-based molecule, and detecting binding of the antibody-based molecule to a pathological Tau protein conformer in the sample from the subject. Assays for carrying out the detection of a pathological Tau protein in a biological sample are well-known in the art and include, without limitation, ELISA, immunohistochemistry, Western blot, etc.

Alternatively, detecting the presence of a pathological Tau protein conformer in a subject using the antibody-based molecule of the present invention can be achieved using in vivo imaging techniques. In vivo imaging involves administering to the subject the antibody-based molecule having antigenic specificity for a pathological Tau peptide and detecting binding of the antibody-based molecule to the pathological Tau protein conformer in vivo.

The antibody-based molecule of the present invention can be administered by injection (e.g., intravenous injection, intracarotid injection, etc.) into the body of the patient, or directly into the brain by intracranial injection. The dosage of such molecule should be from about 0.0001 mg/kg to about 100 mg/kg, and more usually from about 0.01 mg/kg to about 10 mg/kg, of the host body weight. For example, dosages can be about 1 mg/kg body weight or about 10 mg/kg body weight or within the range of about 1-10 mg/kg.

For diagnostic purposes, the antibody-based molecule of the present invention is labeled. Alternatively, in some methods, the molecule may be unlabeled and a secondary labeling agent is used to bind to such molecule (coupled or conjugated either directly to the molecule or indirectly, through an intermediate (such as, for example, a linker known in the art) using techniques known in the art). The choice of label depends on the means of detection. For example, a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, is suitable for optical detection. Chemoluminescent labels may also be employed (e.g., luminol, luciferase, luciferin, and aequorin). Such diagnosis and detection can also be accomplished by coupling the antibody-based molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels and radioisotopic labels can also be employed, and are preferably detected using Positron Emission Tomography (PET) or Single-Photon Emission Computed Tomography (SPECT). Radiolabels include, but are not limited to, bismuth ($^{213}$Bi), carbon ($^{11}$C, $^{13}$C, $^{14}$C), chromium ($^{51}$Cr), cobalt ($^{57}$Co, $^{60}$Co), copper ($^{64}$Cu), dysprosium ($^{165}$Dy), erbium ($^{169}$Er), fluorine ($^{18}$F), gadolinium ($^{153}$Gd, $^{159}$Gd), gallium ($^{68}$Ga, $^{67}$Ga), germanium ($^{68}$Ge), gold ($^{198}$Au), holmium ($^{166}$Ho), hydrogen ($^{3}$H), indium ($^{111}$In, $^{112}$In, $^{113}$In, $^{115}$In), iodine ($^{121}$I, $^{123}$I, $^{125}$I, $^{131}$I), iridium ($^{192}$Ir), iron ($^{59}$Fe), krypton ($^{81m}$Kr), lanthanum ($^{140}$La), lutetium ($^{177}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr), promethium ($^{149}$Pm), rhenium ($^{186}$Re, $^{188}$Re), rhodium ($^{105}$Rh), rubidium ($^{81}$Rb, $^{82}$Rb), ruthenium ($^{82}$Ru, $^{97}$Ru), samarium ($^{53}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb $^{175}$Yb, $^{177}$Yb) yttrium ($^{90}$Y) and zinc ($^{65}$Zn); positron emitting metals using various positron emission tomographies, and non-radioactive paramagnetic metal ions (such as paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$ $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$). Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581; 4,735,210; 5,101,827; 5,102,990; 5,648,471 and 5,697,902, which are hereby incorporated by reference in their entirety. For example, a radioisotope may be conjugated by a chloramine-T method (Lindegren et al. "Chloramine-T In High-Specific-Activity Radioiodination Of Antibodies Using N-Succinimidyl-3-(Trimethylstannyl)Benzoate As An Intermediate," *Nucl. Med. Biol.* 25(7):659-665 (1998); Kurth et al. "Site-Specific Conjugation Of A Radioiodinated Phenethylamine Derivative To A Monoclonal Antibody Results In Increased Radioactivity Localization In Tumor," *J. Med. Chem.* 36(9):1255-1261 (1993); Rea et al. "Site-specifically radioiodinated antibody for targeting tumors," *Cancer Res.* 50(3 Suppl): 857s-861s (1990), which are hereby incorporated by reference in their entirety).

Diagnosis is performed by comparing the number, size, and/or intensity of labeled pathological Tau conformers, Tau aggregates, and/or neurofibrillary tangles in a sample from the subject, or in the subject, to corresponding baseline values. The base line values can represent the mean levels in a population of non-diseased individuals. Baseline values can also represent previous levels determined in the same subject.

Tauopathies that can be detected and diagnosed in accordance with this aspect of the present invention include, without limitation, Pick's disease, progressive supranuclear palsy, corticobasal degeneration, argyrophilic grain disease, primary age-related Tauopathy, globular glial Tauopathy, frontotemporal dementia, parkinsonism linked to chromosome 17, chronic traumatic encephalopathy, Huntington's disease, Amyotrophic Lateral Sclerosis (ALS), Niemann-Pick-C, Guam-ALS-Parkinson's dementia, post-encephalitic Parkinson's disease, aluminum toxicity, and prion disease.

The diagnostic methods described above can also be used to monitor a subject's response to therapy. In this embodiment, detecting the presence of pathological Tau in a subject is determined prior to the commencement of treatment. The level of pathological Tau in the subject at this time point is used as a baseline value. At various times during the course of treatment the detection of pathological Tau protein conformers, Tau aggregates, and/or neurofibrillary tangles is repeated, and the measured values thereafter compared with the baseline values. A decrease in values relative to baseline signals a positive response to treatment. Values can also increase temporarily in biological fluids as pathological Tau is being cleared from the brain.

The present invention is further directed to a kit for performing the above-described diagnostic and monitoring methods. Typically, such kits contain the antibody-based molecule of the present invention. The kit can also include a detectable label. The antibody-based molecule itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring pathological Tau protein in a biological sample, the antibody-based molecule of the kit may be supplied pre-bound to a solid phase, such as to the wells of a microtiter dish.

The presence of labeled Tau antibody-based molecule may be detected in vivo for diagnosis purposes. In one embodiment, such diagnosis comprises: a) administering to a subject an effective amount of such labeled antibody-based molecule; b) waiting for a time interval following administration in order to allow the labeled antibody-based molecule to concentrate at sites (if any) of aggregated Tau and to allow unbound labeled molecule to be cleared to a background level; c) determining a background level; and d) detecting such labeled antibody-based molecule in the subject, such that detection of labeled molecule above the background level is indicative that the subject has a Tauopathy, or is indicative of the severity of such Tauopathy. In accordance with such embodiment, the antibody-based molecule is labeled with an imaging moiety suitable for detection using a particular imaging system known to those skilled in the art. Background levels may be determined by various methods known in the art, including comparing the amount of labeled molecule detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

Therapeutic Utility of the Tau-Binding Antibody-Based Molecules

As indicated above, one aspect of the present invention relates to a method of preventing or treating Alzheimer's disease or other Tauopathy in a subject via the administration of an effective amount of the Tau antibody-based molecule or polynucleotide encoding the Tau antibody-based molecule of the present invention in an amount effective to prevent or treat such Alzheimer's disease or other Tauopathy. Such administration may be provided in order to promote the clearance of Tau aggregates from the brain of a subject or may be provided in order to slow a tangle-related behavioral phenotype in a subject. Additionally, such administration may be provided prophylactically in order to delay, impede, attenuate or prevent the onset of Alzheimer's disease, or other Tauopathy.

Tauopathies that can be treated with the antibody-based molecule or polypeptide encoding the same include, without limitation, Pick's disease, progressive supranuclear palsy, corticobasal degeneration, argyrophilic grain disease, primary age-related Tauopathy, globular glial Tauopathy, frontotemporal dementia, parkinsonism linked to chromosome 17, chronic traumatic encephalopathy, Huntington's disease, Amyotrophic Lateral Sclerosis (ALS), Niemann-Pick-C, Guam-ALS-Parkinson's dementia, post-encephalitic Parkinson's disease, aluminum toxicity, and prion disease.

The term "treatment" or "treating" as used herein means ameliorating, slowing or reversing the progress or severity of a disease or disorder, or ameliorating, slowing or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount," of the antibody-based molecule refers to an amount sufficient, at dosages and for periods of time necessary, to achieve an intended biological effect or a desired therapeutic result including, without limitation, clinical results. The phrase "therapeutically effective amount" when applied to an antibody-based molecule of the invention is intended to denote an amount of the antibody that is sufficient to ameliorate, palliate, stabilize, reverse, slow or delay the progression of a disorder or disease state, or of a symptom of the disorder or disease. In an embodiment, the method of the present invention provides for administration of the antibody-based molecule in combinations with other compounds. In such instances, the "effective amount" is the amount of the combination sufficient to cause the intended biological effect.

An amount adequate to accomplish therapeutic or prophylactic treatment is defined, respectively, as a therapeutically effective dose or a prophylactically effective dose. In both prophylactic and therapeutic regimes, agents are usually administered in several dosages until a sufficient immune response has been achieved. Typically, the immune response is monitored and repeated dosages are given if the immune response starts to wane. A therapeutically effective or prophylactically effective dose of such an antibody or epitope-binding fragment thereof may vary according to factors such as the disease state, age, sex, and weight of the individual, and the ability of the molecule to elicit a desired response in the subject. A therapeutically effective amount is also one in which any toxic or detrimental effects of the antibody or antibody portion are outweighed by the therapeutically beneficial effect.

Patients amenable to treatment include individuals having Alzheimer's disease or such other Tauopathy who show clinically recognized symptoms or indications of such conditions, as well as patients not presently showing symptoms of such conditions. Although Alzheimer's disease is definitively diagnosed only by post-mortem biopsy, individuals suffering from Alzheimer's disease are clinically diagnosed using the Alzheimer's Disease and Related Disorders Association ("ADRDA") Criteria (Carrillo, M. C. et al. "Revisiting The Framework Of The National Institute On Aging-Alzheimer's Association Diagnostic Criteria," *Alzheimers Dement.* 9(5):594-601 (2013); Budson, A. E. et al. "New Criteria For Alzheimer Disease And Mild Cognitive Impairment: Implications For The Practicing Clinician," *Neurologist* 18(6):356-363 (2012); Sarazin, M. et al. "Clinical And Research Diagnostic Criteria For Alzheimer's Disease," *Neuroimaging Clin. N. Amer.* 22(1):23-32 (2012); Husain, M. M. "Clinical Diagnosis And Management Of Alzheimer's Disease," *Neuroimaging Clin. N. Amer.* 15(4):767-777 (2005), which are hereby incorporated by reference in their entirety). Such individuals can alternatively be distinguished from those having diseases or conditions that are un-related to Alzheimer's disease or other Tauopathy by the presence of correlated risk factors (i.e., one or more factors that have been found to possess greater than 50% coincidence with Alzheimer's disease or such other Tauopathy). Such correlated risk factors include the finding that a patient has had relatives who have experienced Alzheimer's disease or such other Tauopathy, or present a family history of hypercholesterolemia or atherosclerosis. Such correlated risk factors particularly include the finding that a patient possesses one or more genetic or biochemical markers that have been correlated with (i.e., found to possess greater than 50% coincidence with) the occurrence of such actual disease. Examples of such genetic markers of risk toward Alzheimer's disease include correlated mutations in the APP gene, for example, mutations at position 717 and positions 670 and 671 of the APP gene (referred to as the Hardy and Swedish mutations respectively). Other suitable markers of known genetic risk include correlated mutations in the presenilin genes (PS1 and PS2) and in the ApoE4 gene (Bekris, L. M. et al. "Genetics of Alzheimer Disease," *J. Geriatr. Psychiatry Neurol.* 23(4):213-227) (2010), which is hereby incorporated by reference in its entirety).

PS1 mutations associated with genetic risk of Alzheimer's disease include the substitutions: R35Q; A79V; V82L; L85P; V89L; V94M; V96F; V97L; F105I; F105L; F105V; L113P; L113Q; Y115C; Y115D; Y115H; T116I; T116N; P117A; P117L; P117R; P117S; E120D; E120D; E120G; E120K; E123K; N135D; N135S; A136G; M139I; M139I; M139K; M139T; M139V; I143F; I143M; I143N; I143T; I143V; M146I; M146I; M146I; M146L; M146L; M146V; T147I; L153V; Y154C; Y154N; H163R; H163Y; W165C; W165G; L166H; L166P; L166R; S169L; S169P; S170F; L171P; L173F; L173W; L174M; L174R; F175S; F177L; F177S; S178P; G183V; E184D; V191A; G206A; G206D; G206S; G206V; G209E; G209R; G209V; S212Y; I213F; I213L; I213T; H214D; H214Y; G217D; G217R; L219F; L219P; Q222H; Q222R; Q223R; L226F; L226R; I229F; A231T; A231V; M233I; M233L; M233L; M233T; M233V; L235P; L235V; F237I; F237L; K239N; T245P; A246E; L248R; L250S; L250V; Y256S; A260V; V261F; V261L; L262F; C263F; C263R; P264L; G266S; P267L; P267S; R269G; R269H; L271V; V272A; E273A; T274R; R278I; R278K; R278S; R278T; E280A; E280G; L282F; L282R; L282V; P284L; P284S; A285V; L286P; L286V; T291P; E318G; R358Q; S365A; R377M; G378E; G378V; L381V; G384A; F386S; S390I; V391F; L392P; L392V; G394V; N405S; A409T; C410Y; V412I; L418F; L420R; L424F; L424H; L424R; L424V; A426P; A431E; A431V; A434C; L435F; P436Q; P436S; and I439S.

PS2 mutations associated with genetic risk of Alzheimer's disease include the substitutions: R29H; G34S; R62C; R62H; R71W; A85V; T122P; T122R; S130L; V139M; N141I; L143H; V148I; R163H; M174V; S175C; Y231C; Q228L; M239V; M230I; A252T; P334R; T430M; and D439A.

ApoE4 alleles are associated with risk of Alzheimer's disease (Verghese et al. "Apolipoprotein E In Alzheimer's Disease And Other Neurological Disorders," *Lancet Neurol.* 10(3):241-252 (2011), which is hereby incorporated by reference in its entirety).

In addition, a number of diagnostic tests are available for identifying individuals who have Alzheimer's disease. These include measurement of CSF Tau and A042 levels. Elevated Tau and decreased AB42 levels signify the presence of Alzheimer's disease.

In the case of Alzheimer's disease, virtually anyone is at risk of suffering from Alzheimer's disease. Therefore, the therapeutic molecules of the present invention can be administered prophylactically to the general population without the need for any assessment of the risk of the subject patient. The present methods are especially useful for the prophylactic treatment of individuals who do have a known genetic risk of Alzheimer's disease. In asymptomatic patients, treatment can begin at any age (e.g., 10, 20, 30). Usually, however, it is not necessary to begin treatment until a patient reaches 40, 50, 60, 70, 80 or 90 years of age. Treatment typically entails the administration of multiple dosages over a period of time. Treatment can be monitored by assaying antibody, or activated T-cell or B cell responses to the therapeutic agent over time. If the response falls, a booster dosage is indicated. In the case of potential Down's syndrome patients, treatment can begin ante-natally by administering the therapeutic agent to the mother during pregnancy or shortly after the patient's birth.

EXAMPLES

Examples are provided below to illustrate the present invention. These examples are not meant to constrain the present invention to any particular application or theory of operation

Example 1—The 8B2D1 Monoclonal Antibody Exhibits Unique Tau Binding Characteristics Peptide Tau 386-408[phospho-serine396,404] (TDHGAEIVYK{pSER}PVVSGDT{pSER}PRHL; SEQ ID NO: 1) was conjugated via a cysteine (c) residue with KLH as immunogen, and 10 BALB/c mice were immunized. All mice showed satisfied immune response and two optimal mice were used for cell fusion and hybridoma production. FIG. 1 shows the binding of dilutions of monoclonal antibody 8B2D1 to its immunogen, referred to as P-Ser396, P-Ser404 (SEQ ID NO: 1) (containing phosphorylated serine residues at positions 11 and 19 of SEQ ID NO: 1), and to Tau peptides having the same amino acid sequence but phosphorylated only on serine 404 (P-Ser404) (serine 19 of SEQ ID NO: 1), or phosphorylated only on serine 396 (P-Ser396) (serine 11 of SEQ ID NO: 1). Binding of the monoclonal 8B2D1 antibody to a non-phosphorylated Tau peptide (No-P) containing this sequence (Tau386-408) was also determined.

The anti-Tau 8B2D1 mAb showed preference for binding to the diphosphorylated peptide (P-Ser396, P-Ser404), but also bound well to the P-Ser404 peptide and the non-phosphorylated peptide. Negligible binding was detected to the P-Ser396 peptide. Background binding of the cell culture medium (Negative (Medium)) to the individual peptides was very low as well.

Figures 2A, 2B, 2C:
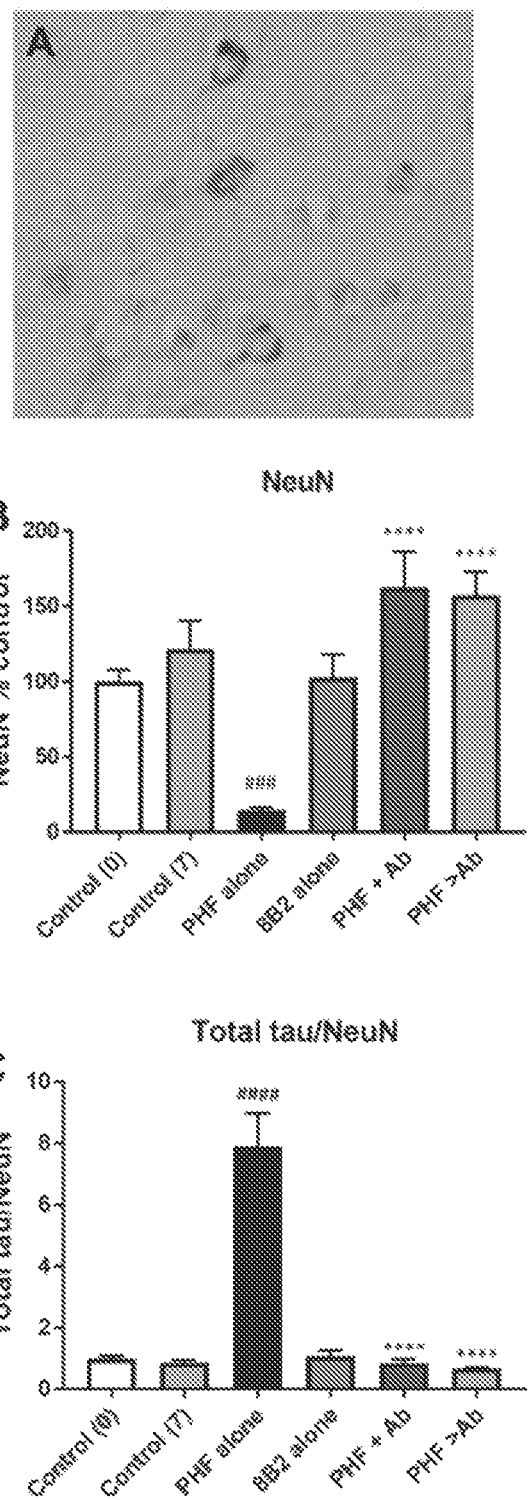
FIGS. 2A-2C show that monoclonal tau antibody 8B2D1 binds to pathological tau protein in human brain tissue (FIG. 2A) and prevents the toxicity and seeding of human brain-derived pathological tau protein in primary neuronal culture (FIGS. 2B and 2C). ###, ####p<0.001, 0.0001 compared to untreated control at 7 days. ****p<0.0001 compared to PHF alone.

The monoclonal anti-tau 8B2D1 antibody also binds to pathological tau protein in human brain tissue and prevents the toxicity and seeding of human brain-derived pathological tau protein in primary neuronal culture. FIG. 2A shows the tau antibody binding to neuronal tau aggregates in fixed human tauopathy brain tissue as detected by immunohistochemistry.

To examine extracellular effects, the anti-Tau 8B2D1 antibody (1 pg/ml) was administered to primary tauopathy JNPL3 mouse neuronal cultures with enriched human paired helical filament pathological tau protein (PHF; 1 pg/ml) derived from human tauopathy brain (PIF+Ab) for 7 days. Under these conditions, the 8B2D1 antibody (Ab) prevents PHIF neurotoxicity as determined by neuron viability (NeuN (neuron nuclei) positive neurons relative to control; FIG. 2B) and clears pathological tau protein (total Tau/Neuron (NeuN); FIG. 2C).

To examine intracellular effects, the anti-Tau 8B2D1 antibody was administered 24 h after PHIF (PIF>Ab), to allow time for the PHIF to be taken up into the neurons. Under these conditions (PIF>Ab), the anti-Tau 8B2D1 antibody also prevents PHIF neurotoxicity (FIG. 2B), and clears tau pathology (FIG. 2C), examined 7 days later, with comparable efficacy to the extracellular condition. Neurons treated with the anti-tau 8B2D1 antibody alone did not differ from controls, and controls at 0 and 7 days did not differ from each other. ###, ####$p<0.001$, $0.0001$ compared to untreated control at 7 days. ****$p<0.0001$ compared to PHIF alone. A total of eight wells of neurons per condition were examined in two separate experiments with comparable results obtained in both experiments.

Figures 3A, 3B, 3C:
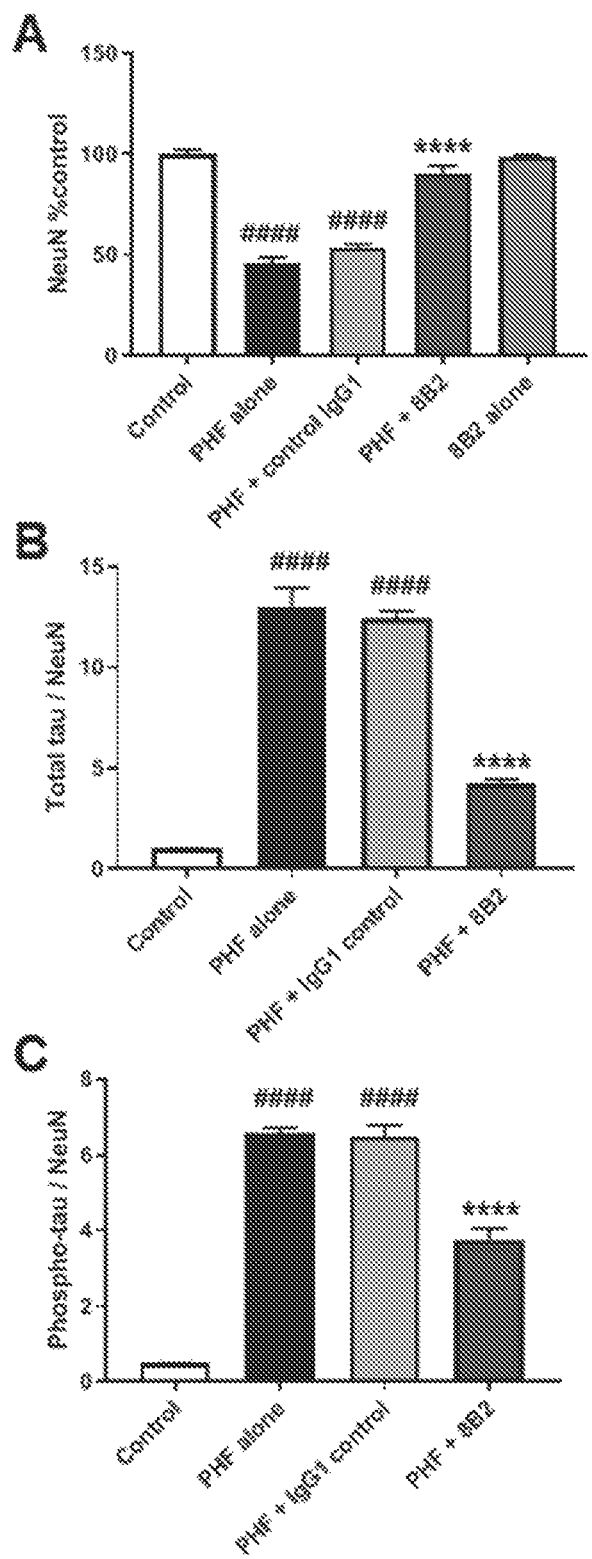
FIG. 3 shows that monoclonal tau antibody 8B2D1 binds to pathological tau protein in mixed primary JNPL3 mouse brain culture and prevents associated toxicity (FIG. 3A) and clears pathological tau (FIG. 3B) and phospho-tau (P-Ser199) (FIG. 3C). ####p<0.0001, compared to control group (untreated). ****p<0.0001 compared to PHF alone or PHF+IgG1 control. A total of six wells of cells per condition were examined.

The monoclonal anti-tau 8B2D1 antibody is also effective in mixed primary JNPL3 mouse brain culture. This culture model contains all brain cell types, including microglia, which may have a role in antibody-mediated tau clearance. Under these conditions, higher dose of PIF is needed for neuronal toxicity, presumably because of trophic and clearance support from other cell types, and the antibody dose is increased accordingly. To examine extracellular effects, tau antibody (10 µg/ml) was administered with human tauopathy PHIF (10 µg/ml) for 4 days. Under these conditions, the 8B2D1 antibody prevents PHIF neurotoxicity (FIG. 3A) and clears pathological tau and phospho-tau (p-Ser199) protein (FIG. 3B-C). Neurons treated with the anti-tau 8B2D1 antibody alone did not differ from controls, and control IgG1 antibody was ineffective. ####$p<0.0001$, compared to control group (untreated). ****$p<0.0001$ compared to PHF alone or PHF+IgG1 control. A total of six wells of cells per condition were examined.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An antibody-based molecule that binds to an epitope of Tau, the epitope present in the Tau sequence of TDHGAEIVYK$^{\{P\}}$SPVVSGDT$^{\{P\}}$SPRHL (SEQ ID NO:1), wherein the antibody-based molecule comprises a heavy chain variable (VH) domain and a light chain variable (VL) domain, the VH domain comprising a heavy chain complementarity-determining region 1 (H-CDR1) comprising the amino acid sequence of SEQ ID NO: 2, a heavy chain complementarity-determining region 2 (H-CDR2) comprising the amino acid sequence of SEQ ID NO: 3, and a heavy chain complementarity-determining region 3 (H-CDR3) comprising the amino acid sequence of SEQ ID NO: 4, and the VL domain comprising a light chain complementarity-determining region 1 (L-CDR1) comprising the amino acid sequence of SEQ ID NO: 5, a light chain complementarity-determining region 2 (L-CDR2) comprising the amino acid sequence of SEQ ID NO: 6, and a light chain complementarity-determining region 3 (L-CDR3) comprising the amino acid sequence of SEQ ID NO: 7.

2. The antibody-based molecule of claim 1, wherein the VH domain comprises the amino acid sequence of SEQ ID NO: 8.

3. The antibody-based molecule of claim 1, wherein the VL domain comprises the amino acid sequence of SEQ ID NO: 9.

4. The antibody-based molecule of claim 1, wherein the antibody-based molecule comprises: a VH domain having the amino acid sequence of SEQ ID NO: 8 and a VL domain having the amino acid sequence of SEQ ID NO: 9.

5. The antibody-based molecule of claim 1, wherein the antibody-based molecule binds to a phosphorylated-Tau protein that comprises the amino acid sequence of SEQ ID NO:1, and wherein serine residues at positions 11 and 19 of SEQ ID NO: 1 are phosphorylated, or only the serine residue at position 19 is phosphorylated.

6. The antibody-based molecule of claim 1, wherein the antibody-based molecule is a full-length antibody, or an epitope-binding fragment of the antibody, or a scFv.

7. The antibody-based molecule of claim 6, wherein the epitope binding fragment is a F(ab), a F(ab'), or a F(ab')2.

8. The antibody-based molecule of claim 1, wherein the antibody-based molecule is a scFv or comprises the scFv.

9. The antibody-based molecule of claim 8, wherein the scFv comprises the amino acid sequence of SEQ ID NO: 18.

10. The antibody-based molecule of claim 1, wherein the VH domain is humanized and comprises human or humanized immunoglobulin heavy chain framework regions.

11. The antibody-based molecule of claim 1, wherein the VL domain is humanized and comprises human or humanized immunoglobulin light chain framework regions.

12. The antibody-based molecule of claim 1, wherein the antibody-based molecule is coupled or conjugated to a detectable label selected from the group consisting of a fluorescent label, a chemiluminescent label, a radioisotope label, a paramagnetic label, a positron-emitting metal label, an enzyme label, a streptavidin/biotin and avidin/biotin; and wherein the enzyme label is selected from the group consisting of a horseradish peroxidase, an alkaline phosphatase, a beta-galactosidase and an acetylcholinesterase.

13. A pharmaceutical composition comprising:
the antibody-based molecule of claim 1 and
a pharmaceutically acceptable carrier.

14. A diagnostic kit comprising: the antibody-based molecule of claim 12.

15. A method of detecting presence of aggregates of phosphorylated- and/or non-phosphorylated-Tau protein in neurons of brain tissue, the method comprising: contacting the neurons isolated from the brain tissue of a human subject with tauopathy with the antibody-based molecule of claim 12, and detecting the presence of accumulated phosphorylated- and/or non-phosphorylated-Tau protein in neurons of the human brain tissue by immunohistochemical staining methods in vitro, wherein the phosphorylated- and/or non-phosphorylated-Tau protein comprises the amino acid sequence of SEQ ID NO:1 and wherein the phosphorylated-Tau protein comprises phosphorylated serine residues at positions 11 and 19 of SEQ ID NO: 1, or only one phosphorylated serine residue at position 19 of SEQ ID NO: 1.

16. An isolated nucleic acid molecule comprising a polynucleotide encoding the antibody-based molecule of claim 1.

17. A vector comprising the isolated polynucleotide of claim 16.

18. An isolated host cell comprising the vector of claim 17.

* * * * *

SEQUENCE LISTING

```
<160> NUMBER OF SEQ ID NOS: 25

<210> SEQ ID NO 1
<211> LENGTH: 23
<212> TYPE: PRT
<213> ORGANISM: Artificial
<220> FEATURE:
<223> OTHER INFORMATION: Tan peptide
<220> FEATURE:
<221> NAME/KEY: MISC_FEATURE
<222> LOCATION: (10)..(18)
<223> OTHER INFORMATION: S at position 11 is phosphorylated residues
<220> FEATURE:
<221> NAME/KEY: MISC_FEATURE
<222> LOCATION: (10)..(18)
<223> OTHER INFORMATION: S at position 19 is phosphorylated residues

<400> SEQUENCE: 1

Thr Asp His Gly Ala Glu Ile Val Tyr Lys Ser Pro Val Val Ser Gly
1               5                   10                  15

Asp Thr Ser Pro Arg His Leu
            20
```

<210> SEQ ID NO 2
<211> LENGTH: 5
<212> TYPE: PRT
<213> ORGANISM: Artificial
<220> FEATURE:
<223> OTHER INFORMATION: heavy chain CDR

<400> SEQUENCE: 2

Ser Tyr Val Ile His
1               5

<210> SEQ ID NO 3
<211> LENGTH: 17
<212> TYPE: PRT
<213> ORGANISM: Artificial
<220> FEATURE:
<223> OTHER INFORMATION: heavy chain CDR

<400> SEQUENCE: 3

Tyr Ile Tyr Pro Tyr Asn Asp Gly Thr Ile Tyr Asn Glu Lys Phe Lys
1               5                   10                  15

Gly

<210> SEQ ID NO 4
<211> LENGTH: 8
<212> TYPE: PRT
<213> ORGANISM: Artificial
<220> FEATURE:
<223> OTHER INFORMATION: heavy chain CDR

<400> SEQUENCE: 4

Glu Arg Asp Asn Tyr Gly Val Tyr
1               5

<210> SEQ ID NO 5
<211> LENGTH: 16
<212> TYPE: PRT
<213> ORGANISM: Artificial
<220> FEATURE:
<223> OTHER INFORMATION: light chain CDR

<400> SEQUENCE: 5

Arg Ser Ser Gln Ser Ile Val His Ser Asn Gly Asn Thr Tyr Leu Glu
1               5                   10                  15

<210> SEQ ID NO 6
<211> LENGTH: 7
<212> TYPE: PRT
<213> ORGANISM: Artificial
<220> FEATURE:
<223> OTHER INFORMATION: light chain CDR

<400> SEQUENCE: 6

Lys Val Ser Asn Arg Phe Tyr
1               5

<210> SEQ ID NO 7
<211> LENGTH: 9
<212> TYPE: PRT
<213> ORGANISM: Artificial
<220> FEATURE:
<223> OTHER INFORMATION: light chain CDR

<400> SEQUENCE: 7

Phe Gln Asp Ser His Ile Pro Tyr Thr
1               5

```
<210> SEQ ID NO 8
<211> LENGTH: 136
<212> TYPE: PRT
<213> ORGANISM: Artificial
<220> FEATURE:
<223> OTHER INFORMATION: heavy chain variable region

<400> SEQUENCE: 8
```

Met Glu Trp Ser Trp Ile Phe Leu Ile Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Ile His Trp Val Lys Gln Lys Pro Gly Gln Gly Leu
    50                  55                  60

Glu Trp Ile Gly Tyr Ile Tyr Pro Tyr Asn Asp Gly Thr Ile Tyr Asn
65                  70                  75                  80

Glu Lys Phe Lys Gly Lys Ala Thr Leu Thr Ser Asp Thr Ser Ser Ser
                85                  90                  95

Thr Val Tyr Met Glu Leu Ile Ser Leu Thr Ala Glu Asp Ser Ala Val
            100                 105                 110

Tyr Trp Cys Val Arg Glu Arg Asp Asn Tyr Gly Val Tyr Trp Gly Gln
        115                 120                 125

Gly Thr Thr Leu Thr Val Ser Ser
    130                 135

```
<210> SEQ ID NO 9
<211> LENGTH: 131
<212> TYPE: PRT
<213> ORGANISM: Artificial
<220> FEATURE:
<223> OTHER INFORMATION: light chain variable region

<400> SEQUENCE: 9
```

Met Lys Leu Pro Val Arg Leu Leu Val Leu Met Phe Trp Ile Pro Ala
1               5                   10                  15

Ser Ser Ser Asp Val Leu Leu Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Glu Leu Leu Ile Tyr Lys Val Ser Asn Arg Phe Tyr
65                  70                  75                  80

Gly Val Pro Asp Arg Phe Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Asp Ser His Ile Pro Tyr Thr Phe Gly Gly Gly Thr Arg Leu
        115                 120                 125

Glu Ile Lys
    130

```
<210> SEQ ID NO 10
<211> LENGTH: 14
<212> TYPE: DNA
```

<213> ORGANISM: Artificial
<220> FEATURE:
<223> OTHER INFORMATION: heavy chain CDR

<400> SEQUENCE: 10
agctatgtta ttca                                                    14

<210> SEQ ID NO 11
<211> LENGTH: 50
<212> TYPE: DNA
<213> ORGANISM: Artificial
<220> FEATURE:
<223> OTHER INFORMATION: heavy chain CDR

<400> SEQUENCE: 11
tatatttatc cttacaatga tggtactatt tacaatgaga aattcaaagg              50

<210> SEQ ID NO 12
<211> LENGTH: 24
<212> TYPE: DNA
<213> ORGANISM: Artificial
<220> FEATURE:
<223> OTHER INFORMATION: heavy chain CDR

<400> SEQUENCE: 12
gagagggata attacggggt ctat                                         24

<210> SEQ ID NO 13
<211> LENGTH: 48
<212> TYPE: DNA
<213> ORGANISM: Artificial
<220> FEATURE:
<223> OTHER INFORMATION: light chain CDR

<400> SEQUENCE: 13
agatctagtc agagcattgt acatagtaat ggaaacacct atttagag                48

<210> SEQ ID NO 14
<211> LENGTH: 21
<212> TYPE: DNA
<213> ORGANISM: Artificial
<220> FEATURE:
<223> OTHER INFORMATION: light chain CDR

<400> SEQUENCE: 14
aaagtttcca accgatttta t                                            21

<210> SEQ ID NO 15
<211> LENGTH: 27
<212> TYPE: DNA
<213> ORGANISM: Artificial
<220> FEATURE:
<223> OTHER INFORMATION: light chain CDR

<400> SEQUENCE: 15
tttcaagatt cacatattcc gtacacg                                      27

<210> SEQ ID NO 16
<211> LENGTH: 408
<212> TYPE: DNA
<213> ORGANISM: Artificial
<220> FEATURE:
<223> OTHER INFORMATION: heavy chain variable region

<400> SEQUENCE: 16

```
atggaatgga gttggatatt tctcattctc ctgtcaggaa ctgcaggtgt ccactctgag      60
gtccagctgc aacagtctgg acctgagctg gtaaagcctg ggcttccgt gaagatgtcc     120
tgcaaggctt ctggatacac attcactagc tatgttattc actgggtgaa gcagaagcct    180
gggcagggcc ttgagtggat tggatatatt tatccttaca atgatggtac tatttacaat    240
gagaaattca aggcaaggc cacactgact tcagacacat cctccagcac agtctacatg     300
gaactcatca gcctgaccgc tgaggactct gcggtctatt ggtgtgtaag agagagggat    360
aattacgggg tctattgggg ccaaggcacc actctcacag tctcctca                 408
```

<210> SEQ ID NO 17
<211> LENGTH: 393
<212> TYPE: DNA
<213> ORGANISM: Artificial
<220> FEATURE:
<223> OTHER INFORMATION: light chain variable region

<400> SEQUENCE: 17

```
atgaagttgc ctgttaggct gttggtgctg atgttctgga ttcctgcttc cagcagtgat     60
gttttgctga cccaaactcc actctccctg cctgtcagtc ttggagatca agcctccatc    120
tcttgcagat ctagtcagag cattgtacat agtaatggaa acacctattt agagtggtac    180
ctgcagaaac aggccagtc tccagagctc ctgatctaca agtttccaa ccgatttat      240
ggggtcccag acaggttcag tggcagtgga tcagggacag atttcacact caagatcagc    300
agagtggagg ctgaggatct gggagtttat tactgctttc aagattcaca tattccgtac    360
acgttcggag gggggaccag gttggaaata aaa                                 393
```

<210> SEQ ID NO 18
<211> LENGTH: 285
<212> TYPE: PRT
<213> ORGANISM: Artificial
<220> FEATURE:
<223> OTHER INFORMATION: Tau ScFv

<400> SEQUENCE: 18

```
Met Lys Leu Pro Val Arg Leu Leu Val Leu Met Phe Trp Ile Pro Ala
1               5                   10                  15

Ser Ser Ser Asp Val Leu Leu Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Glu Leu Leu Ile Tyr Lys Val Ser Asn Arg Phe Tyr
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Asp Ser His Ile Pro Tyr Thr Phe Gly Gly Gly Thr Arg Leu
        115                 120                 125

Glu Ile Lys Ser Ser Gly Gly Gly Gly Ser Gly Gly Gly Gly Gly Gly
    130                 135                 140
```

```
Ser Ser Arg Ser Ser Met Glu Trp Ser Trp Ile Phe Leu Ile Leu Leu
145                 150                 155                 160

Ser Gly Thr Ala Gly Val His Ser Glu Val Gln Leu Gln Gln Ser Gly
            165                 170                 175

Pro Glu Leu Val Lys Pro Gly Ala Ser Val Lys Met Ser Cys Lys Ala
        180                 185                 190

Ser Gly Tyr Thr Phe Thr Ser Tyr Val Ile His Trp Val Lys Gln Lys
    195                 200                 205

Pro Gly Gln Gly Leu Glu Trp Ile Gly Tyr Ile Tyr Pro Tyr Asn Asp
210                 215                 220

Gly Thr Ile Tyr Asn Glu Lys Phe Lys Gly Lys Ala Thr Leu Thr Ser
225                 230                 235                 240

Asp Thr Ser Ser Ser Thr Val Tyr Met Glu Leu Ile Ser Leu Thr Ala
            245                 250                 255

Glu Asp Ser Ala Val Tyr Trp Cys Val Arg Glu Arg Asp Asn Tyr Gly
        260                 265                 270

Val Tyr Trp Gly Gln Gly Thr Thr Leu Thr Val Ser Ser
    275                 280                 285

<210> SEQ ID NO 19
<211> LENGTH: 18
<212> TYPE: PRT
<213> ORGANISM: Artificial
<220> FEATURE:
<223> OTHER INFORMATION: linker

<400> SEQUENCE: 19

Ser Ser Gly Gly Gly Ser Gly Gly Gly Gly Ser Ser Arg
1               5                   10                  15

Ser Ser

<210> SEQ ID NO 20
<211> LENGTH: 28
<212> TYPE: PRT
<213> ORGANISM: Artificial
<220> FEATURE:
<223> OTHER INFORMATION: N-terminal leader sequence

<400> SEQUENCE: 20

Ile Gln Glu Glu Phe Lys Met Lys Lys Thr Ala Ile Ala Ile Ala Val
1               5                   10                  15

Ala Leu Ala Gly Phe Ala Thr Val Ala Gln Ala Ala
            20                  25

<210> SEQ ID NO 21
<211> LENGTH: 15
<212> TYPE: PRT
<213> ORGANISM: Artificial
<220> FEATURE:
<223> OTHER INFORMATION: antibody constant domain

<400> SEQUENCE: 21

Ala Lys Thr Thr Pro Pro Ser Val Thr Ser Gly Gln Ala Gly Gln
1               5                   10                  15

<210> SEQ ID NO 22
<211> LENGTH: 6
<212> TYPE: PRT
<213> ORGANISM: Artificial
<220> FEATURE:
<223> OTHER INFORMATION: histidine tag
```

<400> SEQUENCE: 22

His His His His His His
1               5

<210> SEQ ID NO 23
<211> LENGTH: 12
<212> TYPE: PRT
<213> ORGANISM: Artificial
<220> FEATURE:
<223> OTHER INFORMATION: HA-tag

<400> SEQUENCE: 23

Gly Ala Tyr Pro Tyr Asp Val Pro Asp Tyr Ala Ser
1               5                   10

<210> SEQ ID NO 24
<211> LENGTH: 33
<212> TYPE: PRT
<213> ORGANISM: Artificial
<220> FEATURE:
<223> OTHER INFORMATION: C-terminal peptide portion

<400> SEQUENCE: 24

Ala Lys Thr Thr Pro Pro Ser Val Thr Ser Gly Gln Ala Gly Gln His
1               5                   10                  15

His His His His Gly Ala Tyr Pro Tyr Asp Val Pro Asp Tyr Ala
            20                  25                  30

Ser

<210> SEQ ID NO 25
<211> LENGTH: 441
<212> TYPE: PRT
<213> ORGANISM: Homosapien

<400> SEQUENCE: 25

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

-continued

```
Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
            210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440
```